US011971405B2

United States Patent
Alexandrakis et al.

(10) Patent No.: US 11,971,405 B2
(45) Date of Patent: Apr. 30, 2024

(54) NANOSENSORS AND METHODS OF MAKING AND USING NANOSENSORS

(71) Applicant: Board of Regents, The University of Texas System, Austin, TX (US)

(72) Inventors: Georgios Alexandrakis, Arlington, TX (US); Jon Weidanz, Arlington, TX (US); Muhammad Usman Raza, Arlington, TX (US); Sai Santosh Sasank Peri, Arlington, TX (US)

(73) Assignee: BOARD OF REGENTS, THE UNIVERSITY TEXAS SYSTEM, Austin, TX (US)

( * ) Notice: Subject to any disclaimer, the term of this patent is extended or adjusted under 35 U.S.C. 154(b) by 274 days.

(21) Appl. No.: 16/770,841

(22) PCT Filed: Dec. 11, 2018

(86) PCT No.: PCT/US2018/064999
§ 371 (c)(1),
(2) Date: Jun. 8, 2020

(87) PCT Pub. No.: WO2019/118495
PCT Pub. Date: Jun. 20, 2019

(65) Prior Publication Data
US 2020/0393456 A1     Dec. 17, 2020

Related U.S. Application Data

(60) Provisional application No. 62/597,727, filed on Dec. 12, 2017.

(51) Int. Cl.
G01N 33/543     (2006.01)
B82Y 15/00      (2011.01)
(Continued)

(52) U.S. Cl.
CPC ........ *G01N 33/54373* (2013.01); *B82Y 15/00* (2013.01); *G01N 21/648* (2013.01); *G01N 33/487* (2013.01)

(58) Field of Classification Search
CPC .......... G01N 33/54373; G01N 21/648; G01N 33/487; G01N 33/49; B82Y 15/00
See application file for complete search history.

(56) References Cited

U.S. PATENT DOCUMENTS

2009/0136958 A1   5/2009   Gershow et al.
2012/0258544 A1   10/2012  Chen et al.
(Continued)

OTHER PUBLICATIONS

Pang, et al., "Optical Trapping of 12nm Dielectric Spheres Using Double-Nanoholes in a Gold Film," Nano Lett.; 2011; 11(9), 3763-3767. Aug. 12, 2011 (Year: 2011).*
(Continued)

*Primary Examiner* — Samuel P Siefke
*Assistant Examiner* — Henry H Nguyen
(74) *Attorney, Agent, or Firm* — Maynard Nexsen PC; John P. Zimmer; Candice Cashman

(57) ABSTRACT

In one aspect, molecular sensors and methods of making molecular sensors are described herein. In some embodiments, such a sensor comprises a first layer having a dual nanohole structure and a second layer having at least one nanopore. In some embodiments, the first and second layer define a chip of the sensor. In another aspect, methods of sensing are described herein, which in some embodiments comprise (i) providing a test sample comprising complexed and/or non-complexed biomolecules; (ii) contacting the test sample with the first layer of the molecular sensor; (iii) irradiating the dual nanohole structure of the sensor with a beam of electromagnetic radiation; (iv) optically trapping the biomolecules in the dual nanohole structure and measuring a surface plasmon resonance; (v) applying an electric
(Continued)

field across the nanopore of the sensor; and (vi) measuring change in current across the nanopore during one or more translocation events of the biomolecules.

20 Claims, 14 Drawing Sheets

(51) Int. Cl.
*G01N 21/64* (2006.01)
*G01N 33/487* (2006.01)

(56) References Cited

U.S. PATENT DOCUMENTS

| 2012/0292496 | A1 | 11/2012 | Escobedo et al. |
| 2013/0176563 | A1* | 7/2013 | Ozawa ............. G01N 33/48721 356/301 |
| 2013/0323858 | A1* | 12/2013 | Abdulhalim ..... G01N 33/54373 422/69 |
| 2014/0045277 | A1 | 2/2014 | Gordon et al. |

OTHER PUBLICATIONS

Ghorbanzadeh et al., "Improvement of Sensing and Trapping Efficiency of Double Nanohole Apertures via Enhancing the Wedge Plasmon Polariton Modes with Tapered Cusps", ACS Photonics, 2017, 4, 1108-1113. (Year: 2017).*
Shi et al., "A Scattering Nanopore for Single Nanoentity Sensing", ACS Sens., 2016, 1, 1086-1090 (Year: 2016).*
Crick et al., "Low-Noise Plasmonic Nanopore Biosensors for Single Molecule Detection at Elevated Temperatures", ACS Photonics, 2017, 4, 2835-2842 (Year: 2017).*
Regmi et al., "Nanoscale volume confinement and fluorescence enhancement with double nanohole aperture", 2015, Scientific Reports, 5:15852 (Year: 2015).*
Pang, et al., "Optical Trapping of 12nm Dielectric Spheres Using Double-Nanoholes in a Gold Film," Nano Lett.; 2011; 11(9), 3763-3767. Aug. 12, 2011; Abstract; p. 3764 col. 1; 3764 col. 2; Fig. 1.
Balushi, Double Nanohole Aperture Optical Tweezers: Towards Single Molecule Studies, PhD dissertation, University of Victoria; 2016; p. 25-26; p. 29-30; p. 121; Fig. A.3(b).
International Search Report for PCT/US2018/64999; dated Mar. 18, 2019.

* cited by examiner

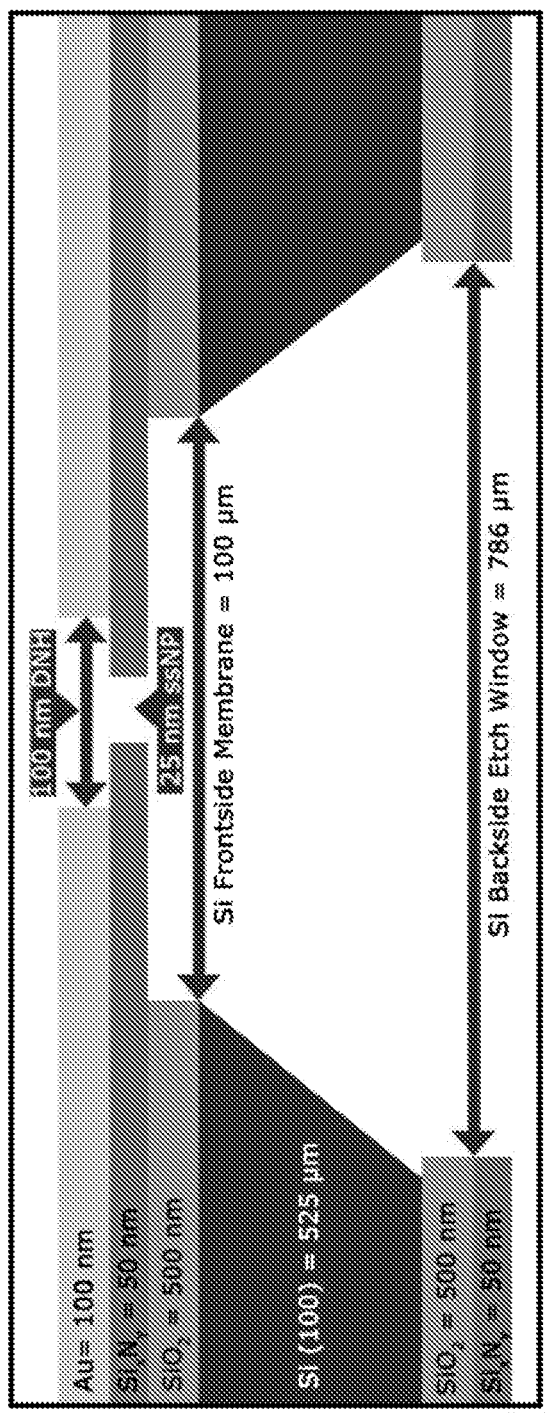
FIG. 7C
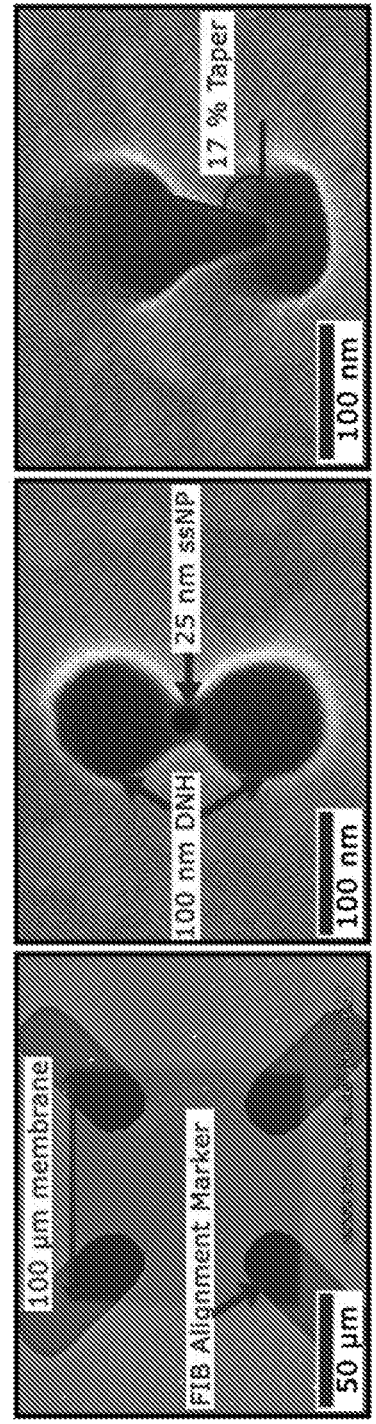
FIG. 7D
FIG. 7E
FIG. 7F

NANOSENSORS AND METHODS OF MAKING AND USING NANOSENSORS

CROSS-REFERENCE TO RELATED APPLICATIONS

This application is a U.S. national phase filing under 35 U.S.C. § 371 to International Patent Application No. PCT/U.S.2018/064,999 filed, Dec. 11, 2018, which claims priority pursuant to 35 U.S.C. § 119(e) to U.S. Provisional Patent Application No. 62/597,727, filed on Dec. 12, 2017, each of which is hereby incorporated by reference in its entirety.

FIELD

This invention relates to sensors and methods of making and using sensors, including for biological applications.

BACKGROUND

The heterogeneity of cancer, polyclonal resistance, development against drugs, and the rise of new genetic mutations make it hard to define precise and tailored therapies to stop disease progression. Existing analytical technologies have contributed greatly in identifying key protein partners that disrupt cancer signaling pathways, like EGFR inhibitors to treat lung cancers. However, these technologies fail to identify how and when certain cancer targets stop responding to specific drugs. For example, some lung cancers are known to become resistant to first generation EGFR inhibitors due to the accumulation of mutations. There is a clear need for point-of-care molecular analysis technologies that can, for instance, identify the best treatment based on an individual tumor protein's ability to interact with a drug, thus providing actionable information to the healthcare provider.

Peptide-presenting MHC receptors being targeted by recombinant TCR-like antibodies can mediate specific cancer cell killing. The current challenge in implementing this therapeutic approach is that cancer cells express a wide variety of such receptors, with each variety only being expressed in a limited number of copies per cell. The large variety of possible targets makes it hard to select the appropriate antibody to target the cancer in each patient. Once such an antibody is identified successfully, though, its targeting can recruit T-cells that will amplify the range of cancer-related peptides presented by other MHC receptors and this amplification effect will wake up the host immune system against the cancer. Current analytical tools for identifying and validating TCR targets include LC/MS/MS based screening of peptide-presenting antigens, FACS sorting of targeted cancer cells, and immunohistochemistry. All these techniques require significant amounts of tumor biopsy (>100 mg), which in many cases are not available from the patient. Other available binding assays that can potentially work at lower protein concentrations use label-free plasmon resonance (e.g. Biacore) or microscale thermophoresis. However, these assays are confounded by the presence of non-specific binding and aggregates, which has limited their use beyond ultra-pure protein solutions. Novel RNA-Seq approaches were also proposed to identify peptide-specific TCRs, but these require further development to meet the demands of personalized clinical applications. The high-specificity systems and methods needed to assess empirically whether a candidate TCR-like antibody will target peptide-presenting MHC ligands in a patient's tumor are not readily available. Thus, there is a clear need for a simultaneously highly sensitive and highly selective detection system/method capable of working at very low concentrations to identify specific peptide/MHC ligand-antibody complexes enriched from a patient's cancer.

SUMMARY

Devices and methods for sensing are described herein. In some instances, devices and methods described herein provide label-free detection using localized plasmon resonance measurements coupled with an electrical sensing nanopore system to dynamically "arrest" individual proteins and protein complexes. In some cases, such proteins or protein complexes are targeted by an inhibitor to determine whether the inhibitor can disrupt complex formation. For example, in some embodiments, devices and methods described herein dynamically arrest individual receptor protein ligand complexes and quantify complex formation.

Additionally, devices and methods described herein can use optical trapping to prevent a protein complex from translocating too quickly through the nanopore. Such optical trapping can also be used to provide further information about a translocating species. In some embodiments, devices and methods described herein enable simultaneous quantification of mass and effective charge. For example, when a molecular complex enters the optical trap, in some cases, step-like signal changes are detected that are in proportion to the molecular complex's mass. Additionally, devices and methods described herein, in some cases, have an electrical sensing mechanism, wherein change in ionic conductivity is recorded when molecular complexes translocate through the nanopore. For example, the amplitude of current change and duration of the change, in some embodiments, provides information about the size and charge of the molecule. Devices and methods described herein can thus provide independent measurements to verify whether protein complex formation is disrupted, or whether a protein complex is formed. Moreover, devices and methods described herein can identify the best treatment based on an individual tumor profile and/or a tumor protein's ability to interact with a drug of interest.

In one aspect, sensors are described herein. In some embodiments, a sensor described herein comprises a first layer having at least one dual nanohole (also referred to as a double nanohole) structure and a second layer having at least one nanopore. The dual nanohole structure comprises a first nanohole and a second nanohole connected by a gap. Additionally, the gap of the first layer is aligned with the nanopore of the second layer. More specifically, the gap and the nanopore are aligned in a direction corresponding to a translocation direction across the first and second layers. Moreover, in some embodiments, the first layer and the second layer are immediately adjacent layers. Alternatively, in other cases, the first layer and the second layer are not immediately adjacent layers but are instead spaced apart by (or adhered together with) one or more adhesion layers. In some such embodiments, the adhesion layer bonds to both the first layer and to the second layer with a greater bonding strength than the first layer and the second layer would bond to one another in the absence of the adhesion layer. Additionally, in some instances, the first layer and the second layer (and the one or more adhesion layers, if present) define a chip of the sensor, such as a unitary or modular chip of the sensor. Moreover, in some cases, a sensor described herein comprises an optional third layer and fourth layer. In some cases, the third and/or fourth layers define a window, including for imaging and/or measurement purposes.

In another aspect, methods of sensing are described herein. In some embodiments, such a method comprises (a) providing a test sample comprising complexed and/or non-complexed biomolecules; (b) contacting the test sample with the first layer of a sensor described herein; (c) irradiating the dual nanohole structure of the first layer of the sensor with a beam of electromagnetic radiation; (d) optically trapping the biomolecules in the dual nanohole structure of the first layer of the sensor and measuring a surface plasmon resonance of the dual nanohole structure; (e) applying an electric field across the nanopore of the second layer of the sensor; and (f) measuring change in current across the nanopore during one or more translocation events of the optically trapped biomolecules.

In yet another aspect, methods of making a sensor are described herein. In some embodiments, the method comprises (a) providing a chip having a first and second layer; (b) forming a dual nanohole structure in the first layer; and (c) forming a nanopore in the second layer, wherein the dual nanohole structure comprises a first nanohole and a second nanohole connected by a gap. The gap is aligned with the nanopore of the second layer in a direction corresponding to a translocation direction across the first and second layers. Additionally, the dual nanohole structure is formed through or in the first layer, but not in or through the second layer.

These and other embodiments are described in more detail in the detailed description which follows.

BRIEF DESCRIPTION OF THE FIGURES

FIG. 7C is a schematic cross-section (profile view) of a sensor described herein.

FIG. 7D is an SEM micrograph of a plan view of a sensor chip prior to focused ion beam drilling.

FIG. 7E is a plan view of a helium ion microscope image of a milled dual nanohole (DNH) with 17% side wall taper and 25 nm solid-state nanopore drilled at its center.

FIG. 7F is a perspective view of a helium ion microscope image of a milled dual nanohole (DNH) with 17% side wall taper and 25 nm solid-state nanopore drilled at its center.

DETAILED DESCRIPTION

Figure 1:
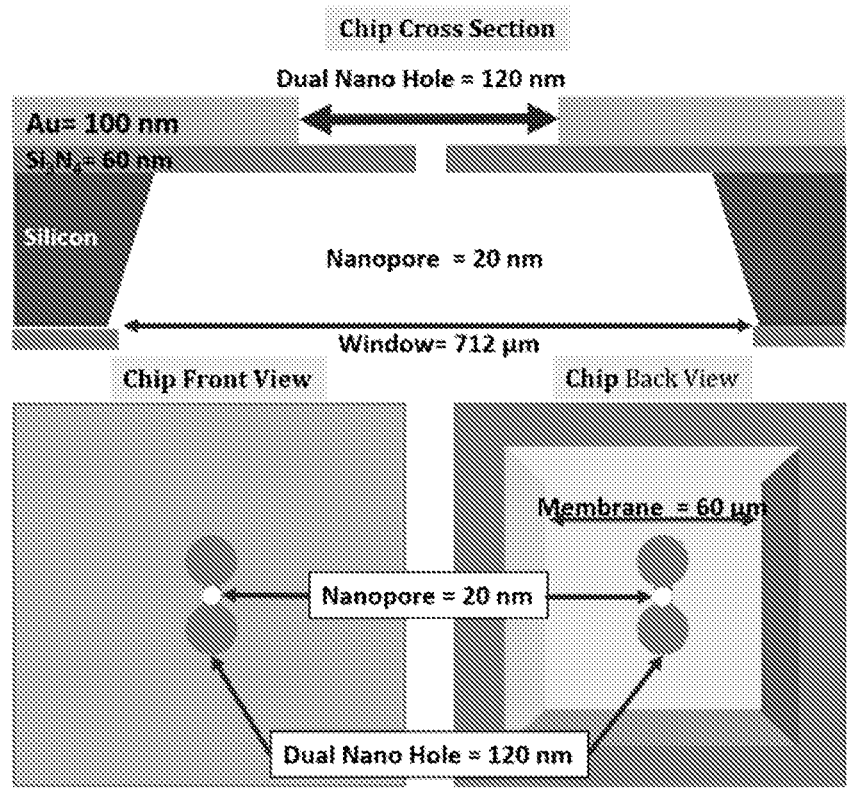
FIG. 1 schematically illustrates the structure of a sensor according to one embodiment described herein. The nanopore is at the middle of the plasmonic gap.

Embodiments described herein can be understood more readily by reference to the following detailed description, examples, and figures. Devices and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Sensors

In one aspect, sensors are described herein. In some embodiments, a sensor described herein is a dual-sensing sensor, having at least two distinct methods of sensing. For example, in some cases, the sensor is both optically and electrically sensing.

A sensor comprises, in some embodiments, a chip or a wafer. The chip or wafer, in some cases, is defined by an xy-plane comprising at least a first layer and a second layer. The first layer, in some embodiments, is essentially parallel to the second layer, which is in contrast to a perpendicular z-direction. The z-direction is a translocation direction that is perpendicular and extending through the xy-plane of the chip or wafer. In some embodiments, the translocation direction goes through the first layer and the second layer of the xy-plane. The translocation direction, in some embodiments, is unidirectional, wherein the first layer is penetrated before the second layer. For example, a translocation direction can correspond to a movement through the chip or wafer from a cis chamber to a trans chamber, wherein the cis chamber is in communication with and, in some instances, partially defined by the first layer, and the trans chamber is in communication with the second layer. In some embodiments, a chip or wafer of a sensor described herein can have a substantially rectangular or square shape. In some cases, a chip or wafer can have a length and/or width of about 5-50 mm, 5-40 mm, 5-30 mm, 10-30 mm, 10-20 mm, or about 15 mm.

In some embodiments, the first layer is positioned superior to the second layer. In some instances, the first and second layer are immediately adjacent layers. In some such embodiments, the first and second layers may be joined or adhered to one another via direct layer/wafer bonding. Alternatively, in other cases, the first layer and the second layer are not immediately adjacent layers but are instead spaced apart by or adhered together with one or more adhesion layers. In some such embodiments, the adhesion layer bonds to both the first layer and to the second layer with a greater bonding strength than the first layer and the second layer would bond to one another in the absence of the adhesion layer. Any adhesion layer not inconsistent with the objectives of the present disclosure may be used in a sensor described herein. For example, in some cases, an adhesion layer is formed from a metal (e.g., an elemental metal or a mixture or alloy of different metals), which may be particularly useful for adhering or bonding a metal first layer to an electrically insulating material second layer described herein, or for adhering or bonding a gold first layer to a silicon nitride second layer as described herein. In some embodiments, a metal adhesion layer can comprise titanium (e.g., elemental titanium metal) or chromium (e.g., elemental chromium metal). Other materials may also be used to form an adhesion layer of a sensor described herein. Further, an adhesion layer can have any thickness or average thickness not inconsistent with the objectives of the present disclosure. For example, in some cases, an adhesion layer has a thickness of up to 50 nm, up to 20 nm, up to 10 nm, or up to 5 nm. In some instances, an adhesion layer described herein has a thickness of about 0.5-20 nm, 0.5-15 nm, 0.5-10 nm, 1-20 nm, 1-15 nm, 1-10 nm, or 1-5 nm. In some embodiments, an adhesion layer can have a thickness of about 0.5-5 nm, 0.5-4 nm, 0.5-3 nm, 0.5-2 nm, or 0.1-1 nm.

Additionally, in some embodiments, the first and/or second layer of a sensor described herein is formed from an inorganic material, such as a metal (which may be an elemental metal or mixture or alloy of metals) or an electrically insulating material, as described further herein below.

Moreover, the first layer, in some cases, functions as an optically sensing layer. In some embodiments, as described above, the first layer is formed from a metal. Any metal not inconsistent with the objectives of the present disclosure may be used. For example, the metal can be an elemental metal or a mixture or alloy of metals. In one embodiment, the first layer is formed from gold. In some instances, a first layer described herein is formed from a different metal. The first layer material is not necessarily particularly limited. In some cases, a specific material is chosen due to its electrical conductivity properties, its chemical inertness in biological systems, and/or its compatibility with device fabrication methods described herein. In another aspect, the first layer has an average thickness of up to 500 nm in the translocation direction. In some embodiments, for example, the first layer has an average thickness of about 5-110 nm, 10-120 nm, 20-130 nm, 30-140 nm, 60-200 nm, 70-300 nm, 80-400 nm, 90-500 nm, or about 50-150 nm in the translocation direction.

Additionally, the first layer, in some embodiments, comprises at least one dual or double nanohole structure, wherein the dual or double nanohole structure comprises a first nanohole and a second nanohole. The first nanohole, in one embodiment, is essentially the same as the second nanohole. In another aspect, the nanoholes of the first layer each have an average diameter in the direction perpendicular to the translocation direction of about 80-150 nm. In other aspects, the nanoholes of the first layer each have an average diameter in the direction perpendicular to the translocation direction of about 100-150 nm, 80-100 nm, 80-120 nm, 90-120 nm, 90-130, or 100-120 nm.

In some embodiments, the nanoholes can have a center-to-center separation distance of about 150 nm or less, and in some cases, the nanoholes can overlap. For example, the nanoholes, in some embodiments, can each have a perimeter drawn by a theoretical line, thereby creating two imaginary circle-like shapes. In some instances, the theoretical lines defining the perimeter shape of each nanohole intersect in one or two locations. When the lines touch or intersect, it is understood that the nanoholes touch or overlap, respectively. In other instances, the theoretical lines defining the perimeter of each nanohole may not touch or intersect. When the lines do not touch or intersect, it is understood that the nanoholes do not touch or overlap. In some cases, the nanoholes can have a center-to-center separation distance of about 50-150 nm, 75-150 nm, 80-140 nm, 80-130 nm, or 100-120 nm.

In another embodiment, the nanoholes can have sloped or tapered interior walls along the translocation direction. The sloped interior walls, in some instances, can have a grade of about 10-30%. For example, the nanoholes can have an interior wall with a downward slope in the translocation direction such that each nanohole is shaped like an inverted cone or a funnel. In some cases, the sloped or tapered walls can have a grade of about 10-20%, 15-20%, or 15-30%.

Moreover, it is to be understood that a "nanohole" described herein can have any shape not inconsistent with the objectives of the present disclosure, including any cross-sectional shape in the xy-plane (perpendicular to the translocation direction). In some embodiments, one or both nanoholes are generally round, circular, ovoid, or ellipsoidal (ignoring any "gap" between the nanoholes, as described above). In other instances, one or both nanoholes have a triangular or other polygonal cross-sectional shape in the xy-plane. The precise shape of a nanohole described herein is not particularly limited. It is further to be understood that the size and/or center-to-center separation of a pair of nanoholes described herein can be selected based on the cross-sectional shape of the nanohole and/or based on the biomolecule analyte to be optically trapped in the dual nanohole structure. In one exemplary embodiment, for instance, two equilateral triangular nanoholes may be used having side lengths of 50-150 nm, wherein vertices of the triangular nanoholes are joined or separated by the gap of the dual nanohole structure.

Figure 7A:
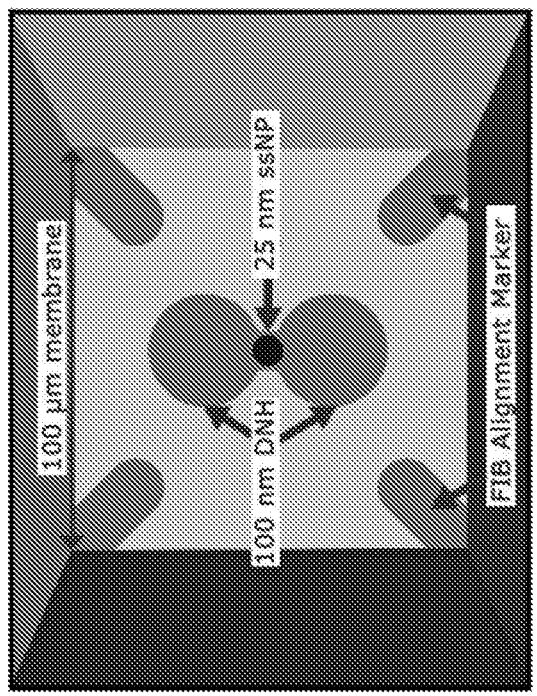
FIG. 7A is a schematic plan view of a sensor described herein.
Figure 7B:
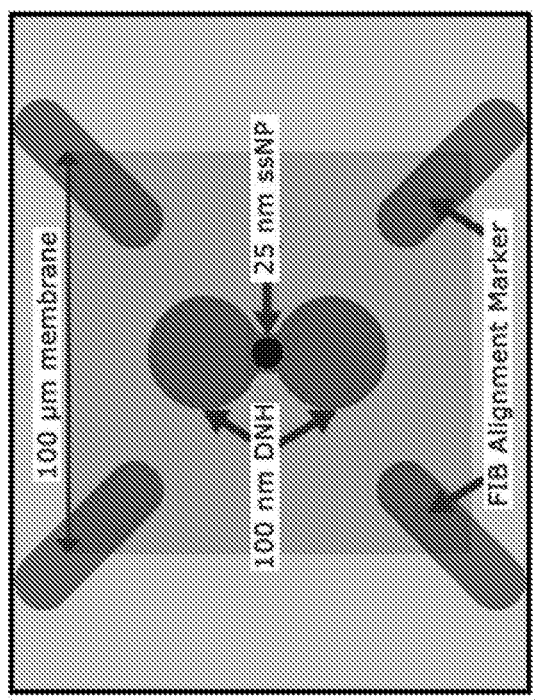
FIG. 7B is a schematic bottom view of a sensor described herein.
Figure 7G:
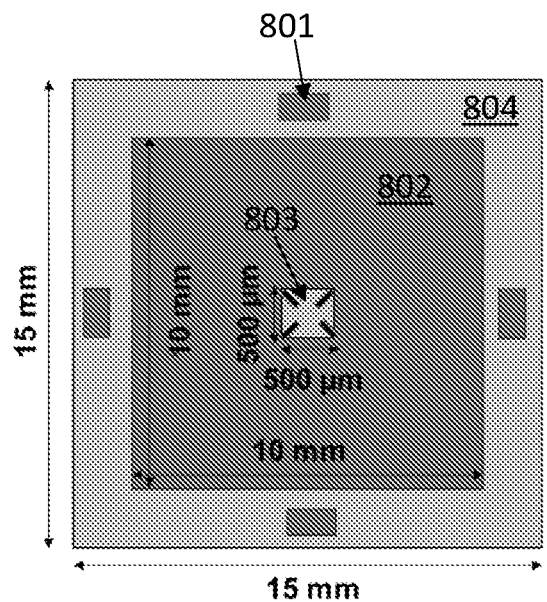
FIG. 7G is a schematic of a sensor, as described herein, with modifications to the gold deposited region.
Figure 7H:
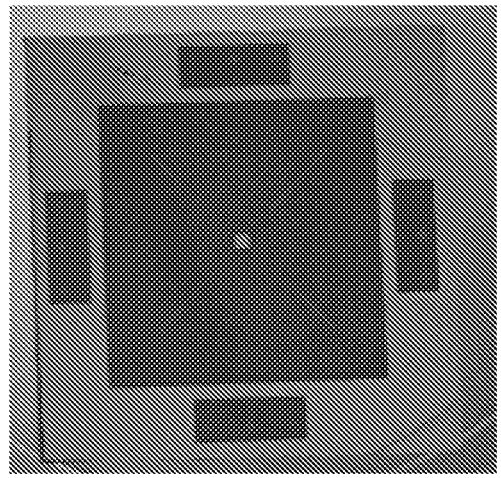
FIG. 7H is a photograph of a fabricated sensor according to the embodiment in FIG. 7G.
Figure 7I:
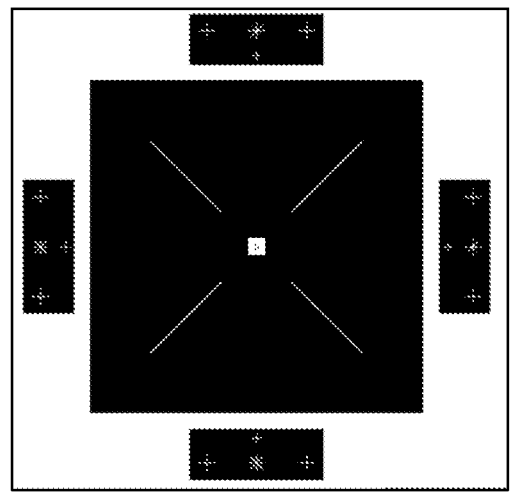
FIG. 7I is a photomask design of the schematic in FIG. 7G.

In some embodiments, the first layer can be non-continuous. As shown in FIG. 7G-7I, a non-continuous first layer can comprise one or more holes and/or areas of the first layer that are etched away, removed, or generally absent, i.e., materially vacant, as depicted by the dark gray shaded or blackened areas. Such a hole 801, removal, or material vacancy of the first layer 802, in some instances, can create one or more areas of the first layer that appear as an island 803 separated from other areas of the first layer 804. Alternatively, or in addition, such a hole 801, removal, or absence of the first layer 802, in some cases, can create a first layer having a Swiss cheese-like pattern. In some cases, where a hole 801 or area of material vacancy in the first layer 802 exists, the second layer can be exposed and/or visible. It should be understood that a non-continuous first layer comprising one or more holes 801 or areas that are etched away or generally absent 802 are in addition to the one or more dual nanoholes, and are substantially larger in diameter and area than the dual nanoholes, e.g., orders of magnitude larger. Furthermore, in some cases, an area of a non-continuous first layer having a hole and/or a material vacancy need not have necessarily had a continuous first layer followed by etching or removal. In some cases, a non-continuous first layer having holes and/or material vacancies can be formed by selective deposition of the first layer.

In some embodiments, a non-continuous first layer comprises a perimeter circumscribing the dual nanohole of the first layer, wherein the perimeter is an edge of the first layer. For example, the perimeter can define an island 803 of the first layer that is separated from other areas of the first layer.

As shown in FIG. 7G-7I, in some embodiments, a geometric perimeter, such as circular, rectangular, or square perimeter, can be defined around the dual nanohole of the first layer. In some cases, one or more areas of the first layer outside the perimeter can be etched away or removed, such that the second layer can be visible through the first layer in the areas where it is etched away or removed, as shown by the dark gray shaded areas of FIG. 7G-7I. In some cases, a first layer perimeter surrounding a dual nanohole structure can have a circumference measuring 1 μm-50 mm, 1 μm-40 mm, 1 μm-30 mm, 1 μm-20 mm, 1 μm-10 mm, or 1 μm-1 mm. In some embodiments, an island 803 in the first layer can have an area of about 1 μm$^2$-100 mm$^2$. In some cases, a hole and/or island 803, as described herein that is not the one or more dual nanoholes in the first layer can have an area of about 100 μm$^2$-100 mm$^2$, 100 μm$^2$-80 mm$^2$, 100 μm$^2$-70 mm$^2$, 100 μm$^2$-60 mm$^2$, 100 μm$^2$-50 mm$^2$, or 100 μm$^2$-40 mm$^2$, 100 μm$^2$-30 mm$^2$, 100 μm$^2$-20 mm$^2$, or 100 μm$^2$-10 mm$^2$, 100 μm$^2$-10 mm$^2$, 100 μm$^2$-5 mm$^2$, 100 μm$^2$-1 mm$^2$, or 100 μm$^2$-0.5 mm$^2$.

Not intending to be bound by theory, it is believed a non-continuous first layer having islands and/or holes, as described above, can reduce metal layer shielding of the externally applied electric field across the sensor, and can increase the electrical conductivity of ionic solution added to the sensor. Consequently, it is believed that a non-continuous first layer can increase the throughput of analytes present in the ionic solution. Additionally, in some cases, such holes and/or selectively deposited areas of the first layer can act as alignment markers.

The second layer, in some embodiments, enables electrical sensing and thus functions as an electrical sensing layer. The second layer is formed from an electrically insulating material in some cases. For example, in one embodiment, the second layer is formed from a silicon nitride. Any silicon nitride not inconsistent with objectives of the present disclosure can be used. In some cases, silicon nitride comprises $Si_xN_y$. In some cases, silicon nitride comprises $Si_3N_4$. In some instances, a second layer described herein is formed from a ceramic material. As described above, such a ceramic material can be electrically insulating. In some embodiments, a second layer described herein is formed from a metal oxide such as a transition metal oxide. In some cases, a second layer described herein is formed from a silicon oxide such as $SiO_2$. Other electrically insulating materials may also be used. The electrically insulating material is not necessarily particularly limited. In some cases, a specific material is chosen due to its electrical conductivity properties, its chemical inertness in biological systems, and/or its compatibility with device fabrication methods described herein. Additionally, the second layer, in some embodiments, has an average thickness of up to 100 nm, or up to 70 nm in the translocation direction. For example, the second layer can have an average thickness of about 5-100 nm, 5-70 nm, 10-70 nm, 20-80 nm, 20-70 nm, 30-120 nm, 30-90 nm, 30-70 nm, 40-100 nm, 40-70 nm, or 50-100 nm in the translocation direction. In addition, the second layer, in some embodiments, comprises at least one nanopore. The nanopore, in one case, has a diameter of at least 5 nm. In other cases, the nanopore has a diameter of about 2-20 nm, 5-25 nm, 15-35 nm, 20-40 nm, or 10-30 nm. In some embodiments, the nanopore is a solid-state nanopore. As understood by one of ordinary skill in the art, a solid-state nanopore is not a biological nanopore, as a solid-state nanopore comprises structural and functional differences that are distinguishable from a biological nanopore.

In some embodiments, the first nanohole and the second nanohole are connected by a gap. The gap as described herein is defined by a continuous hole or opening in the first layer connecting the first nanohole and the second nanohole. The gap, in some instances, is measurable in the x- and y-directions of the xy-plane of the chip. In some instances, the gap defines a line.

In some embodiments, the length and the width of the gap are measured in the xy-plane. In one embodiment, the width and/or length of the gap is defined by a distance between the points of intersection of the theoretical lines defining the perimeter of each nanohole. In some cases, the gap has a width and/or length of about 10-50 nm. In some embodiments, the gap has a width and/or length of about 20-50 nm, 20-40 nm, 30-50 nm, or 20-30 nm.

In some cases, the width and/or length of the gap is defined by the diameter of the nanopore. For example, in some embodiments, the width and/or length of the gap is within 10% of the diameter of the nanopore. Additionally, the gap, in some embodiments, is continuous with the nanopore in the translocation direction. The gap, in other embodiments, has a measurable width and/or length greater than the diameter of nanopore. In other embodiments, the width and/or length of the gap is less than 200% the diameter of the nanopore. In some embodiments the width and/or length of the gap is between 100% and 200% the diameter of the nanopore.

In some embodiments, the center of the gap, determined by its center point in the xy-plane, and the center of the nanopore, also determined by its center point the xy-plane, are aligned in the translocation direction. For example, in some embodiments, the center of the gap of the first layer is aligned with the center of the nanopore of the second layer in a direction corresponding to a translocation direction across the first and second layers, and the centers are spatially separated in the x- or y-direction of the xy-plane by less than 10 nm, or less than 5 nm.

The sensor chip or wafer described herein, in some embodiments, further comprises an optional third layer. The presence of such a layer is preferred in some embodiments. The third layer, in some embodiments is positioned inferior or adjacent to the second layer, such that the second layer is positioned between the first and third layers. The third layer, in some embodiments, can act as an electrically insulating layer that is secondary or supplemental to the second layer, which is also an insulating layer. Thus, the third layer, in some embodiments, can be formed from an electrically insulating material. For example, in some cases, the third layer can comprise or be formed from silicon dioxide ($SiO_2$). In some instances, a third layer described herein is formed from an electrically insulating material described hereinabove, such as a ceramic material or transition metal oxide. Other electrically insulating materials may also be used. The electrically insulating material of the third layer is not particularly limited. In some cases, a specific material is chosen due to its electrical conductivity properties, its chemical inertness in biological systems, and/or its compatibility with device fabrication methods described herein. Not intending to be bound by theory, it is believed that, in some instances, the third layer, which can act as an insulating layer, can contain leakage or prevent the passage of current through any additional layers present beyond the second layer of the chip (in the "downward" direction in FIG. 7C, for instance). In some embodiments, a third layer can have an average thickness of at least 50 nm, at least 100 nm, or at least 500 nm. In some instances, a third layer can have an average thickness of 100-5000 nm, 100-1000 nm, or 100-500 nm.

In some embodiments, the sensor chip or wafer described herein can comprise a fourth layer positioned inferior or adjacent to the third layer, such that the third layer is positioned between the second and fourth layers. Alternatively, the fourth layer can be positioned adjacent the second layer in the absence of a third layer. The fourth layer, in some embodiments, comprises or is formed from silicon. For example, in some cases, the fourth layer can be formed from pure silicon. Other semiconducting materials may also be used. In some embodiments, the fourth layer can act as a semiconducting layer. The fourth layer, in some instances, can have an average thickness of about 1-1000 μm, 10-1000 μm, 50-1000 μm, or 50-500.

In some embodiments, the sensor chip or wafer described herein can comprise one or more layers in addition to the third and fourth layers, such that the fourth layer is positioned between the second or third layer and the one or more additional layers. For example, in some instances, one or more additional layers comprising silicon, including pure silicon, silicon dioxide, and/or silicon nitride can be used. Such additional layers can have an average thickness of about 1-1000 μm, 100-1000 μm, 200-800 μm, 300-600 μm, or about 500 μm.

In some cases, the third layer, fourth layer, and/or additional layers can define a window or an opening "beneath" the first and second layers (e.g., "downward" in FIG. 7C), including a window that extends through the third, fourth, or additional layers, when present. The window, in some cases provides a passage way in the translocation direction from the nanohole of the second layer into a trans chamber of the sensor. Additionally, in some instances, the one or more layers can have sloped or tapered walls in the translocation direction. The sloped walls can have a cone-like shape that taper in the opposite direction of the sloped walls of the nanoholes of the first layer. For example, a distance measured across the window opening in an xy-plane of a layer near the nanopore is smaller than a distance measured across the window opening in an xy-plane of the a layer farthest from the nanopore.

II. Methods of Sensing

The present disclosure additionally provides methods of sensing. A method of sensing described herein can be carried out using any number of embodiments of the sensor device previously described in Section I. Accordingly, in some embodiments, one or more methods of sensing, as described herein, comprises dual sensing. For example, in some cases, methods of sensing comprises both optical and electrical sensing, which, in some instances, are performed simultaneously, or substantially simultaneously. Sensor devices, as described above in Section I, can enable such methods of dual sensing.

In some embodiments, the method comprises (a) providing a test sample comprising complexed and/or non-complexed biomolecules; (b) contacting the test sample with the first layer of a sensor described herein; (c) irradiating the dual nanohole structure of the first layer of the sensor with a beam of electromagnetic radiation; (d) optically trapping the biomolecules in the dual nanohole structure of the first layer of the sensor and measuring a surface plasmon resonance of the dual nanohole structure; (e) applying an electric field across the nanopore of the second layer of the sensor; and (f) measuring change in current across the nanopore during one or more translocation events of the biomolecules.

In one embodiment, the method of sensing comprises providing a test sample comprising complexed and/or non-complexed biomolecules. Complexed and/or non-complexed biomolecules can include, but is not necessarily limited to, exosomes, endosomes, micelles, nucleotides, proteins, lipids, and/or carbohydrates. The biomolecules can be, in some instances, complexed with one or more secondary biomolecules. Exemplary secondary biomolecules may include, but are not limited to small molecules, nucleotides, oligonucleotides, aptamers, proteins, antibodies, lipids, and/ or carbohydrates. The secondary biomolecules, in some embodiments, may be of similar origin as the complexed and/or non-complexed biomolecules. In another embodiment, the secondary biomolecules may be of different origin than the complexed and/or non-complexed biomolecules. For example, a secondary biomolecule may be derived from different species or other foreign organism. In other instances, the biomolecules can be complexed with non-biological molecules. Non-biological molecules may include, but are not limited to any kind of pharmaceutical, such as an antibody, a recombinant protein, a small molecule, or other synthetic product. In some embodiments, a test sample is provided in an ionic solution, such as a salt solution. Any ionic or salt solution not inconsistent with the objectives of the disclosure can be used, including NaCl, KCl, or $CaCl_2$) solution.

Methods of sensing described herein comprise contacting the test sample with the first layer of the sensor. In some cases, the test sample is provided in a chamber positioned cis of a translocation direction. For example, a cis chamber can be positioned adjacent and/or superior to a first layer of a chip of the sensor, as described in Section I, such that placing or positioning the test sample in the cis chamber comprises contacting the test sample with the first layer of the sensor.

In one embodiment, the first layer of the sensor is the optically sensing layer. When the first layer of the sensor is the optically sensing layer, it is expected that the test sample is subjected to the optically sensing layer of the sensor before being subjected to other layers of the sensor.

In some embodiments, a method of sensing comprises irradiating the dual nanohole structure of the first layer with a beam of electromagnetic radiation. Irradiating the dual nanohole can comprise irradiating with a laser beam or laser light (or other suitable electromagnetic radiation). In some cases, the laser beam can be polarized circularly and/or linearly prior to focusing on the dual nanohole structure. In some cases, linearly polarized light is preferred for impingement on the dual nanohole structure. Additionally, in some instances, the laser beam can be focused on the dual nanohole structure using one or more mirrors. The wavelength of electromagnetic radiation used is not necessarily limited. In some embodiments, the laser beam or other electromagnetic radiation comprises visible light or has a wavelength (or average wavelength) centered in the visible region of the electromagnetic spectrum, such as between 450 nm and 750 nm, 500 nm and 700 nm, or 550 nm and 650 nm. In some cases, the laser beam or other electromagnetic radiation comprises infrared (IR) light or has a wavelength (or average wavelength) centered in the IR region of the electromagnetic spectrum. For example, in some instances, a laser beam described herein has a wavelength centered in the near-IR (NIR, 750 nm-1.4 µm), short-wavelength IR (SWIR, 1.4-3 µm), mid-wavelength IR (MWIR, 3-8 µm), or long-wavelength IR (LWIR, 8-15 µm). Moreover, in some embodiments, a laser beam or other electromagnetic radiation described herein has an emission profile/wavelength distribution overlapping with a wavelength at which water and/or biological tissue has an absorption minimum, such as a wavelength between about 700 nm and about 800 nm or between about 1.25 µm and about 1.35 µm.

In another aspect, the method of sensing comprises optically trapping the biomolecules in the dual nanohole structure and/or the gap of the first layer of the sensor and measuring a surface plasmon resonance of the dual nanohole structure. Optical trapping, in some embodiments, is a result of irradiating the dual nanohole structure of the first layer of the sensor with the beam of electromagnetic radiation. Thus, in methods of sensing described herein, a step of optically trapping the biomolecules is performed prior to and/or during a step of irradiating the dual nanohole structure. In some instances, the optical trapping lasts for at least 1 microsecond and less than 100 seconds. In some embodiments, optical trapping lasts for about 1 millisecond-60 sec, 1 millisecond-30 sec, 1 millisecond-10 sec, 1 millisecond-5 sec, 1 millisecond-5 sec, or 10 millisecond-5 sec.

In some embodiments, a step of optically trapping the biomolecules and measuring a surface plasmon resonance can comprise one or more optical trapping events. In some cases, an optical trapping event represents the optical trapping of a single non-complexed or complexed biomolecule. In other cases, an optical trapping event represents the optical trapping of more than one complexed or non-complexed biomolecule. For example, in some cases an optical trapping event can include optical trapping of a first biomolecule followed by optical trapping of a second biomolecule, wherein the second biomolecule is optically trapped with the first biomolecule. It should be understood that optically trapping a first non-complexed biomolecule and a second non-complexed biomolecule is not the same as optically trapping a complexed biomolecule.

In some instances, optically trapping the biomolecules results in a measurable surface plasmon resonance. Wherein a first biomolecule is optically trapped, a first surface plasmon resonance can be measured. Wherein a second biomolecule is optically trapped with a first biomolecule, a second surface plasmon resonance can be measured. In some instances, a first plasmon resonance measured from the first optically trapped biomolecule can be subtracted from the second plasmon resonance measurement to obtain information related to the second biomolecule. In some embodiments, the surface plasmon resonance provides information about the mass of an optically trapped biomolecule. Therefore, measuring the surface plasmon resonance, in some embodiments, comprises measuring the mass of the optically trapped biomolecule. Furthermore, in some embodiments, optically trapping comprises slowing or delaying the translocation of the biomolecules. Such a slowing or delaying can provide greater resolution to the sensing mechanisms of sensors described herein.

In another embodiment, the method of sensing comprises applying an electric field across the nanopore of the second layer of the sensor. The electric field, in some embodiments, is provided by placing patch clamp electrodes in the cis and trans chambers of the sensor, as described above in Section I, or any other electrical sensor with pico- to fempto-ampere ionic current reading sensitivity. Thus, in some cases, applying an electric field across the nanopore can comprise applying an electric field from the cis chamber to the trans chamber of the sensor. In some embodiments, applying an electric field comprises applying a 10-1000 mV bias. In some cases, applying an electric field comprises applying a 10-500 mV, 50-500 mV, 100-500 mv, or about 250 mV bias. In some cases, the voltage can be applied across the sensor as a DC or AC field. For example, in some embodiments, an AC field of frequencies up to 1 GHz can be applied to Ag/AgCl electrodes by an external function generator and detected by Axopatch electronics.

In some embodiments, the electric field is temporarily reversed. For example, in some cases, the electric field is applied from the trans chamber to the cis chamber. Temporary reversal of the electric field is sometimes performed to prevent clogging, or a build-up of biomolecules, at the nanopore and/or the dual nanohole structure and/or gap.

In one embodiment, applying an electric field across the nanopore results in one or more translocation events of the biomolecules. In another embodiment, applying the electric field generates a measurable current across the nanopore. In one aspect, a translocation event results in a detectable change in current across the nanopore. A translocation event, as described herein, comprises the entry and exit of a biomolecule through the nanopore.

In another aspect, the method of sensing comprises measuring change in current across the nanopore during one or more translocation events. For example, in some embodiments, the one or more translocation events result in a detectable change in current across the nanopore. In one embodiment, the one or more translocation events of biomolecules includes biomolecules that were first optically trapped. In another embodiment, the one or more translocation events of the biomolecules includes biomolecules that were not first optically trapped. In some embodiments, the change in current provides information about the charge of the translocating biomolecule. For example, measuring change in current across the nanopore, in some embodiments, comprises measuring the charge of the translocating biomolecule. In another embodiment, the change in current provides information about the relative size of the translocating biomolecule. For example, measuring the change in current across the nanopore, in some embodiments, comprises determining the size of the translocating biomolecule. Wherein a first biomolecule and a second biomolecule are simultaneously optically trapped, translocation of the first biomolecule and second biomolecule, in some cases, can be detected as the sum of the change in current across the nanopore from the translocation of the first and second biomolecules.

In some instances, the test sample may oscillate or "bob" between or within the sensing layers. Such oscillation or bobbing can, in some cases, result in substantially simultaneous sensing from the first and second layers, wherein electrical sensing can be triggered due to proximity of the optical sensing layer, and thereby, optical and electrical sensing signals can be simultaneously recorded. For example, a biomolecule that has entered the optical trap of the first layer and is oscillating between the sensing layers during optical trapping can also be detected by electrical sensing of the second layer. Moreover, the electrical sensing of the second layer can be triggered during optical sensing and both optical and electrical sensing can be terminated upon complete translocation, i.e., exit of the biomolecule from the optical trap and through the nanopore.

Not intending to be bound by theory, it is believed that such test sample oscillation can result from opposing optical and electrical forces of the sensor. Thus, in some cases, one or more steps of sensing methods described herein, such as applying an electric field across the nanopore, can comprise controlling, speeding, delaying, slowing down, or reversing the translocation of the biomolecules. Again not intending to be bound by theory, it is further believed that such oscillation or bobbing can provide one or more advantages related to molecular discrimination of the captured biomolecules. For example, the peak of the bobbing frequency spectrum depends on the properties of the captured molecules. Thus, information recorded during molecular bobbing/oscillation can, in some embodiments, distinguish between two non-interacting molecules captured simultaneously versus a complex of two bound molecules. Additionally, such bobbing can obviate the need of applying precisely timed alternating voltage sequences to force molecules to make multiple transits through the sensor. This can improve the signal to noise ratio and detection of time-dependent variations in molecular kinetics.

In another embodiment, the method of sensing further comprises determining whether the biomolecule is complexed. For example, the information provided from optically trapping the biomolecule and the translocation of the biomolecule, in some embodiments, is used to determine whether or not the biomolecule is complexed.

In still further embodiments, the method of sensing can comprise comparing one or more measurements from a first test sample to one or more measurements from a second test sample. For example, in some instances a first test sample of biomolecules can be provided and measured followed by providing and measuring a second test sample of biomolecules. Measurements of the second sample can be compared to measurements of the first sample to elucidate information about the first and/or second test sample.

In some embodiments, methods of sensing described herein provide for detecting or sensing biomolecules at a milli- ($10^{-3}$), micro- ($10^{-6}$), nano- ($10^{-9}$), pico- ($10^{-12}$), femto- ($10^{-15}$), or atto- ($10^{-18}$) molar concentration of the biomolecules.

III. Methods of Making a Sensor

In another aspect, methods of making a sensor are described herein. A method of making a sensor described herein can be carried out to make a sensor device having any number of the features or characteristics of the sensor previously described in Section I. In some embodiments, the method comprises (a) providing a chip or wafer having a first and second layer; (b) forming a dual nanohole structure in the first layer; and (c) forming a nanopore in the second layer, wherein the dual nanohole structure comprises a first nanohole and a second nanohole connected by a gap, the gap being aligned with the nanopore of the second layer in a direction corresponding to a translocation direction across the first and second layers, and wherein the dual nanohole structure is formed through the first layer and not the second layer.

In some embodiments, the chip is formed from inorganic materials. In one example, the first layer is formed from metal. As a further example, the first layer can be formed from gold. The second layer, in some embodiments, is formed from an electrically insulating material. As an example, the second layer, in one embodiment, can be formed from silicon nitride. Any silicon nitride not inconsistent with objectives of the disclosure can be used. For example, in some cases, the second layer can be formed from $Si_xN_y$. In some cases, the second layer can be formed from $Si_3N_4$.

In other embodiments, the chip comprises a first and second layer. In one embodiment the first and/or second layer each have an average thickness of up to 500 nm. In some cases, the first layer and/or second layer can each have an average thickness of about 5-500 nm, about 10-500 nm, or about 50-100 nm.

In another embodiment, the first layer and the second layer are immediately adjacent layers. In some embodiments, the first and second layer are separated only by an adhesion layer, as described in Section I hereinabove.

In one embodiment, the method comprises forming a dual nanohole structure in the first layer. In another embodiment, the dual nanohole structure is formed in the first layer and not the second layer. In yet another embodiment, the dual nanohole structure comprises a first nanohole and a second nanohole. In one aspect, the method comprises forming the first nanohole followed by marking a traceable location for the first nanohole. In another aspect, the method comprises forming the second nanohole according to the marked location of the first nanohole. In some cases, forming the second nanohole comprises overlapping the second nanohole with the first nanohole. In such cases, forming the second nanohole can further comprise forming a gap. The gap, in some embodiments, is defined by a continuous hole or opening through the first layer connecting the first and second nanoholes. When forming the second nanohole further comprises forming a gap, the gap is understood to be the space where the first and second nanoholes overlap or touch. In some embodiments, forming a dual nanohole is performed using neon focused ion beam milling (FIB), wherein the neon FIB mills the first layer and not the second layer.

In another embodiment, the method comprises forming a nanopore in the second layer. In one embodiment, the nanopore is aligned with the gap of the first layer in a direction corresponding to a translocation direction across the first and second layers, as described in Section I. Thus, in some instances, the nanopore is formed in the second layer after the dual nanohole is formed in the first layer. Moreover, in some cases, the nanopore is formed in the second layer after the gap is formed in the first layer.

In another embodiment, forming the nanopore in the second layer further comprises forming a gap in the first layer. The gap, in some embodiments, is continuous with the nanopore in the translocation direction. In further embodiments, forming the nanopore can further comprise increasing a length and/or width of the gap in first layer. In some embodiments, forming a nanopore is performed using transmission electron microscopy. In some embodiments, forming a nanopore is performed using helium focused ion beam (FIB) milling, wherein the helium focused ion beam mills the second layer and not the first layer.

In other embodiments the method further comprises providing a third layer and, optionally, a fourth layer, wherein the third layer is formed from an electrically insulating material, such as silicon dioxide, and the optional fourth layer is formed from silicon. In some embodiments, the fourth layer defines a window. Thus, in some cases, providing a fourth layer can further comprise providing a window. In some instances, additional layers can also be provided. Additional detail of the third, fourth, and additional layers can be found hereinabove in Section I.

In some embodiments, a method of making a sensor further comprises forming one or more additional holes in the first layer. In some cases, forming additional holes in the first layer can comprise forming a non-continuous first layer, as described hereinabove in Section I. It should be understood that any feature, characteristic, or description of a non-continuous first layer, as described above in Section I, can be present, or can be formed, when performing a step of forming one or more additional holes in the first layer.

In some embodiments, forming one or more additional holes in the first layer can further comprise forming one or more islands in the first layer. For example, an island of first layer material can be formed by etching away, removing, or selectively depositing first layer material. It should be understood that a sensor, as described herein, comprising one or more islands should have a dual nanohole structure positioned on or within an island. Additional detail of first layer islands can be found above in Section I.

In some embodiments, methods of making a sensor further comprise providing an optical assembly and an electrical assembly. An optical assembly can comprise a laser for directing electromagnetic radiation to the dual nanohole and an optical detector for measuring the surface plasmon resonance of the dual nanohole structure. In some embodiments, an optical assembly can further comprise additional components, as described below in the Examples. An electrical assembly can comprise a flow cell for directing current across the nanopore and a patch clamp for measuring change in current across the nanopore. In some embodiments, an electrical assembly can further comprise additional components, as described below in the Examples.

Example 1

Presented herein is a novel approach to simultaneously implement two biosensing modes of biosensors onto a single solid-state chip for nanoscale biomolecular sensing. Optical plasmonic sensing through a dual nanohole structure is utilized with the electrical sensing of a solid-state nanopore. The fabrication of the dual nanohole-nanopore device is presented with the details of processing steps.

Biomolecules such as DNA, RNA, miRNA, proteins, etc. are the building blocks of life. Analysis and quantification of these biomolecules lead to better understanding of the biological processes of the human body. Early detection of life threatening diseases such as cancer can reduce mortality rates drastically. Studies to detect gene mutation and abnormal expression of biomarkers can help in early cancer detection. Many nanoscale techniques have evolved over the past half-century to analyze minute changes in biomolecule concentrations or functions. The detection of size, function, and charge changes of biomolecules has immense diagnostic potential.

Solid-state nanopore is one such nanoscale biosensor that utilizes electrophoresis of a charged molecule across a nanometer membrane to identify a biomolecule. As a biomolecule translocates through a nanopore, there is a drop in the ionic current. A negative spike is witnessed in the ionic current. (Alternatively, a positive spike can be observed in the ionic current, e.g., when a biomolecule enters the nanopore, depending on the isoelectric point of the molecule and pH of the ionic solution.) The translocation time and the amount of the current change from each molecule passing through the nanopore is measured. In this example is a solid-state nanopore in a silicon nitride membrane. Plasmonic resonance is used to trap biomolecules in metal cavities on top of glass substrates. The nanometer scale of the dual nanohole (DNH) cavity results in strong gap plasmonic trapping energy. This traps the proteins or other biomolecules in the cavity. The trapped protein in the gap cavity provides a spike in the optical transmission. This spike is due to the size of the protein trapped inside the cavity. However, plasmonic trapping can be used only to measure the size of the biomolecule. This disclosure utilizes the optical sensing of the DNH cavity and the electrical sensing of the solid-state nanopore on a single chip Devices described herein can have solid-state nanopores and DNHs on a single chip in a bilayer, and in some embodiments, can provide a way of dual modality sensing (FIG. 1). In some embodiments, the biomolecules can be trapped at the mouth of the nanopore and kept there for several microseconds by harnessing the gap plasmon trapping force. This can help, for example, in label-free DNA sequencing without optical tweezers to control the translocation speed of the DNA. The trapping force of the gap plasmon, for example, can provide a means to control the translocation of the DNA through the nanopore and thus sequence it at a set pace. In some embodiments, the size determination of the biomolecule can be accomplished by optical trapping in the DNH gap cavity. For example, a negative spike in translocation current in the solid-state nanopore shows the charge displaced by the biomolecule of interest. Thus, in some embodiments, size and charge of translocating biomolecules are determined in tandem through dual modality electro-optic sensing of the bilayer biosensor.

The sensor is fabricated in a double side polished (100) plane silicon wafer. A 400 nm thin silicon nitride layer is deposited on the wafer using low pressure chemical vapor deposition (LPCVD) system. This is followed by patterning the window on one side of the wafer. The patterned side is exposed to $CF_4$ plasma deep reactive-ion etching (DRIE) for 220 seconds. This etched the silicon nitride all the way through to the silicon. A photoresist layer was coated on the other side as a protective layer against etchant gases during DRIE. Photoresist is removed in an acetone bath.

In another embodiment of the sensor, an optional 0.5-1 µm layer of silicon dioxide can first be deposited on both sides of a double side polished wafer using wet thermal oxidation, followed by deposition of 60-70 nm of either stoichiometric or non-stoichiometric low stress silicon nitride by low pressure chemical vapor deposition (LPCVD) system. This is followed by patterning of window on one side of the wafer. This patterned side is exposed to $CF_4$ plasma deep reactive-ion etching (DRIE) for 100 seconds. This etched the silicon nitride until the oxide layer on the wafer. The oxide layer is removed using buffered oxide etchant that exposes the silicon layer beneath. The other side is coated with a photoresist layer to avoid any etching during nitride and oxide etching processes and removed later using acetone.

Thin Bilayer Chip Fabrication

The patterned wafer is immersed in a 25% diluted tetramethylammonium hydroxide (TMAH) solution at 90° C. for anisotropic etch of the silicon. The etch rate of silicon in (100) plane is ~1 µm/minute. It took ~10 hours for the wet etch to completely etch the silicon through. A 5 nm film of titanium is evaporated on the front side followed by a 100 nm film of gold using an e-beam evaporator at a 0.5 Å/sec deposition rate. The wafer is diced into individual chips (15 mm×15 mm). These chips were placed back side up in a $CF_4$ RIE to etch the silicon nitride to a thickness of 60-70 nm. The bilayer stack is then ready for FIB drilling.

In another embodiment of the sensor, after anisotropic etching of silicon using TMAH solution, a 5 nm film of chromium followed by a 100 nm film of gold is deposited using an e-beam evaporator at deposition rates of 0.5 Å/sec and 1 Å/sec respectively. Chromium is used as an adhesion layer. The gold side is patterned with four alignment markers that will be used as reference markers for focused ion beam drilling. In the patterned regions, gold and chromium are etched using wet etchants. The wafer is diced into individual chips. Each chip is placed into a solution of buffered oxide etch to remove the sacrificial oxide layer beneath the silicon nitride to create the bilayer stack for FIB drilling.

Controlled Drilling of Bilayer

Figure 2:
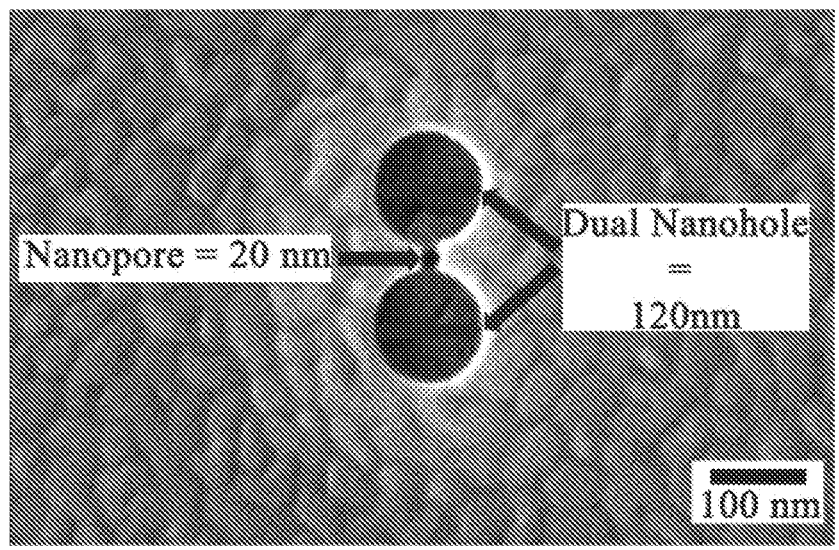
FIG. 2 illustrates an image of the dual nanohole structure (each nanohole having a diameter of 120 nm) with a nanopore (20 nm diameter) aligned with the gap in the middle. The top/first layer is formed from gold and includes the dual nanohole structure. The bottom/second layer is formed from silicon nitride and includes the nanopore.
Figure 3:
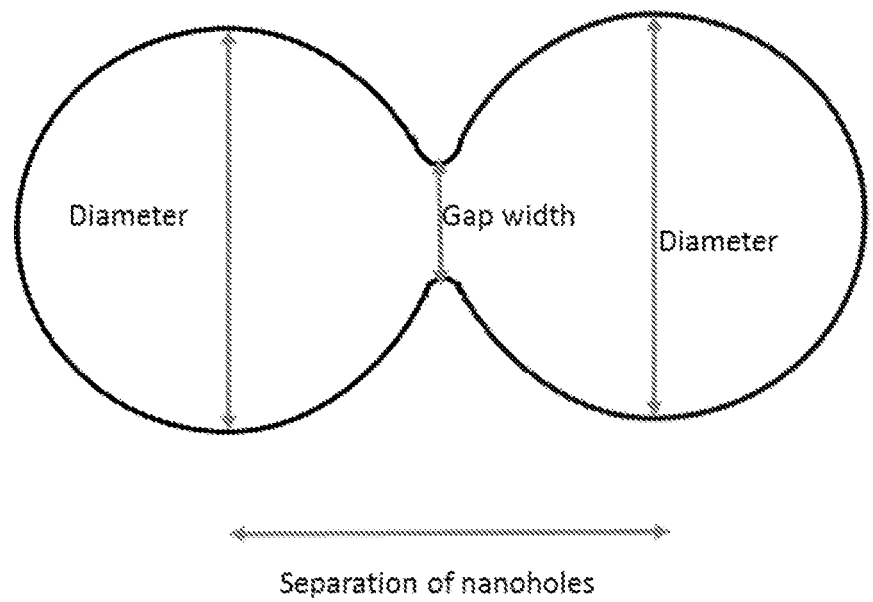
FIG. 3 schematically illustrates a dual nanohole structure according to one embodiment described herein. The measurable nanohole diameter, separation distance of the nanoholes, and the gap width are shown.

A gas field ion source (GFIS) helium ion focused ion beam (FIB) is used to drill pores at two levels. The GFIS helium ion FIB can etch holes as small as 2-3 nm. This is a major advantage above gallium ion FIB which is unable to reach the precision required for the dual nanohole-nanopore system. The control afforded by the helium ion FIB resulted in the desired shape of the sidewalls of the DNH. The DNH had almost vertical walls and the etch stopped exactly at the metal/semiconductor interface. This showed a very good aspect ratio of the etched product. Using a diffraction free FIB source by using a 10 µm aperture size resulted in drilling 20 nm nanopores without etching the sidewalls of the DNH gap cavity. This highly selective drilling resulted in a 20 nm nanopore drilled in the middle of the 30 nm gap cavity in the gold film DNH as shown in FIG. 2.

In another embodiment of the sensor, the double nanohole-nanopore structure is drilled using two different ion sources, neon and helium of the GFIS FIB. The double nanohole structure is created in the gold layer using a neon beam. The neon beam is characterized to create a side wall taper by controlling the beam characteristics such as current, acceleration voltage, aperture and working distance. Neon beam drilling is terminated when the secondary electron current metal dielectric interface. The nanopore structure is drilled using helium ion beam at the center of the double nanohole structure.

After the fabrication of the biosensor chip, the chip is sandwiched in a transparent PDMS assembly with liquid chambers on both sides of the chip. The chambers can be filled with ionic solution and biomolecules introduced.

The PDMS assembly can be fabricated in steps. First step consists of a thick PDMS layer ranging between 1-3 mm in which a pattern is cut. The pattern consists of two square openings connected by a rectangular channel. Second step is bonding PDMS layer to a glass slide and placing the sensor on one of the square openings. Third step is bonding a thin PDMS layer of 200-250 µm to a 1-2 µm cover slip and a square opening is made in this layer. This coverslip with PDMS layer is placed on the sensor to complete the PDMS assembly.

In these embodiments optical and electrical signals are captured using a data acquisition device. This data is processed into to electrical and optical traces. The electrical trace contains alternating current which can be filtered in to a power spectrum frequency which can be used to differentiate between trapped particles. In this manner, it is possible to detect drop in electric current, enhancement in optical transmission and change in frequency of power spectrum when particle is trapped and translocate though the sensor.

Conclusions

The present disclosure describes a novel approach to integrate optical nanoholes and electrical nanopore sensors to achieve dual modality for the selective and error-free detection of disease biomarkers. The system can be utilized for many types of biological molecules. The precision at the nanoscale to fabricate dual-level structures allows interrogation of both size and charge of molecules of interest.

Example 2

As cancer therapy evolves towards personalized interventions, targeted treatments, such as inhibitors, need to consider a patient's pre-treatment biomarkers. There is a growing need for molecular analysis technologies that can verify if a biomarker of interest is indeed targeted by the proposed inhibitor for an individual patient. Successful implementation of such technologies will spare cancer patients from unnecessary treatments as well as proactively offer more effective treatment options that enable a positive outcome and extend life, while reducing health care costs.

Current personalized treatment decisions are often made based on a patient's cancer genetic profile. For example, in non-small cell lung carcinoma (NSCLC) patients who do not over-express EGFR mutants, PD-1 blockade therapy could help extend the life of these patients. However, as the cancer evolves to greater heterogeneity, effective second-line treatment choices remain limited. It would be very useful for the oncologist to have a point-of-care diagnostic to verify that the intended first-line treatment will be effective in a particular patient. Moreover, the same diagnostic can be used to assess and identify a broader panel of drug candidates that could serve as second-line treatments once resistance develops. High-specificity tools to empirically assess whether a patient will respond to treatment are not readily available, which forms the scientific premise of the technology disclosed here. Briefly, most current protein-ligand interaction quantification technologies, whether using label-free plasmon resonance (e.g. Biacore), or contrast agents (e.g. protein microarrays) suffer from non-specific binding to surfaces of immobilized targets and cannot ensure the functional integrity of proteins on surfaces. More recently, microscale thermophoresis is proposed as an alternate for quantifying protein interactions, but this method requires fluorescent tags and protein aggregates that can confound analysis of protein-protein interactions. Other analytical technologies such as deuterium-hydrogen exchange (DHX) combined with mass spectrometry can show if a drug has hit the targeted pocket of a protein, but this process requires time-sensitive manipulations and is cumbersome. This example demonstrates the feasibility of using a label-free sensor technology to assess protein-drug interactions. This novel sensor and approach avoids the commonly seen issues with aggregates and non-specific binding to surfaces that current assays face, while providing a point of care diagnostic to clinicians for assessing treatment efficacies. Described herein are proof of principle experiments for demonstrating that the tyrosine kinase inhibitor Gefinitib disrupts formation of EGFR/phospho-antibody complexes for EGFR isolated from the lysate of cells over-expressing its WT or a mutant form. Successful implementation of this EGFR model provides a framework for development as a clinical decision-making diagnostic to guide personalized treatment decisions for cancer patients. The device described herein can be used in table-top equipment in a clinical laboratory using a patient sample, e.g. a blood draw, to test blocking efficacy.

Current approaches for quantifying molecular interactions using light at near-infrared wavelengths rely on the concentration of light intensity at small volumes in which molecules are trapped by the field gradient. Traditionally, this is achieved by optical tweezers that require high trapping powers (100s of mW), which can lead to sample overheating. More recently, nanosensors were used to create highly-confined intensity hotspots to achieve trapping with lower excitation powers (few mW) while also allowing efficient heat dissipation to avoid sample damage. When a molecular complex enters the trap the detected step-like signal changes are in proportion to its mass. Other methods of high sensitivity molecular mass sensing use whispering gallery mode resonators. This approach enables very high Q-factors, and therefore high mass resolution, but at the price of ever-increasing resonator sizes that suffer from non-specific settling of molecules, which decreases measurement sensitivity. Open resonant cavities with lower Q-factors can be easier to use when handling liquid solutions within the open cavity. Using this technology at single protein levels remains challenging due to the required nm-level control of cavity wall jitter. The design of the optical trapping component of the sensing device described here is based on dual-nanohole arrays with various sensor geometries. The sensor described herein is one of the localized plasmon resonance modes (wedge mode) creating the very intense field in its center that can trap proteins down to ~2.5 nm in size.

A common theme in electrical sensing through a nanopore is that a change in ionic conductivity is recorded as the molecule of interest translocates through the pore and the amplitude of current change and duration of change provide information about the size and charge of that molecule. In the case of proteins that are negatively charged the concomitant ionic current reduction depends on the protein, as well as the pore size, solution pH, and solvent molarity. With appropriate controls the effect of these additional variables could be estimated to yield an effective mass-charge metric for the protein. The dual optical-electrical sensing devices and methods described herein allow the mass of the protein and/or protein complexes to be measured by the optical sensing, while simultaneously allowing the electrical sensing component to determine the charge of the complex. Other simultaneous optical and electrical sensing of molecules either use fluorescence to observe electric translocation of DNA through a nanopore, or use an optical tweezer to measure the electrical force with which a DNA strand is pulled though a nanopore, whereas the present disclosure provides simultaneous quantification of protein complex mass and effective charge.

The present disclosure provides a framework for a nanobiosensing diagnostic that can be used to empirically determine whether a patient's tumor will respond to a proposed treatment. By selecting the best treatment option based on an individual's response to the therapy, this clinical decision support tool can be critical to inform life-saving treatment decisions, while enhancing quality of life and reducing health care costs. Described herein is the quantification of the level of inhibition of phosphorylation at a specific site of the target protein, EGFR, at the single molecule level. The present technology is highly relevant for a number of cancers, as it can be used to empirically determine the binding efficiency of various inhibitors, like EGFR inhibitors, that can be used to target proteins that regulate cancer pathways.

The present disclosure provides simultaneous electrical and optical sensing at the single molecule level that allows separating mass from effective charge estimates in individual proteins and complexes they form without requiring expensive labeling techniques. This is in contrast to other technologies that assume protein mass, wherein the resulting mass estimate bias propagates to the effective charge estimate used to identify that a protein complex had formed.

The present disclosure resolves solution heterogeneity, thus enabling quantification of the fraction of instances when the inhibitor does actually inhibit binding to the trapped protein versus when it does not, rather than having one averaged reading. As a result, applications of the present invention may be able to detect the onset of treatment resistance earlier, compared to sample-averaged methods, as cancer cells are treated continually with the same inhibitor.

The present disclosure prevents clogging of the sensor by implementing real-time diagnostics of the optical and electrical signal in LabVIEW to enable quick reaction times to reduce the possibility of clogging. The optical signal changes drastically when undesired agglomerates settle over the central pore of the sensor, which will enable implementing an immediate field polarity reversal that will push these away before the pore is blocked. It is much easier to unclog a pore if the aggregate settling is recent.

The present disclosure provides working with low protein concentrations in the pM range as it can attract and enrich for protein complexes from solution continually. In contrast, other optical trapping devices and methods using localized plasmons require high µM concentrations because the trapping volume is nanoscopic and it can take a long time for a protein to diffuse into that volume. This higher concentration requirement is price-prohibitive for some proteins.

The present disclosure provides differentiation of proteins that are actually bound together versus those that simply co-exist inside the same trap space by using frequency modulation of the light field intensity forming the optical trap.

Described herein are the specifications that define being able to test the efficacy of an inhibitor at the single protein level with higher specificity using an integrated nano-biosensing technology capable of detecting mass and charge simultaneously, while preventing agglomerate issues. The present disclosure can provide empirical information on the efficacy of treatments, thus informing critical, life-saving treatment decisions as the cancer evolves. Additional embodiments can include multiplexed optical-electrical sensors on a wafer. Multiplexing provides higher data throughput for improving estimates of an inhibitor's specificity and allows testing of multiple inhibitors at the same time.

Described herein is a sensor for trapping a wide range of protein sizes (5-500 kDa) and methods of sensing for stable optical trapping and simultaneous optical-electrical measurements in model solutions. Also described herein are characterizations of the bimodal sensor's mass and effective charge measurement sensitivity. Provided herein are methods to perform bound fraction measurements of anti-EGFR aptamers (WT and mutant) targeting WT EGFR in pure solution, and methods of detecting the effect of the tyrosine kinase inhibitor Gefitinib on the bound fraction of a phospho-antibody targeting WT and mutant EGFR captured from cell lysates, followed by MS-based validation.

Nanofabrication of the sensing platform: Optical trapping occurs at the center of a dual-nanohole structure drilled through a 100 nm Au layer by focused ion beam (FIB) milling (FIG. 1a). The He and Ne ion beams provide milling precision (<5 nm) appropriate for the sensor dimensions disclosed here. The dual-nanohole sensor geometry without a nanopore at its center traps single protein molecules. Step-like signal increases are seen when a protein is trapped near the central nanogap due to coupling of light from a wedge-mode plasmon into the far field. FIB milling provides controlling nano-feature sizes and the slope of walls carved within the Au layer. TDFD simulations (Lumerical) provide candidate geometries maximizing the optical trapping force in the wedge-mode. The methods and/or devices described herein include functional sensors that can be further configured as needed in a given instance. The optical sensing system using the nanofabricated sensors described herein demonstrates the capacity of trapping a single 10 nm bead (FIG. 7).

Figure 4:
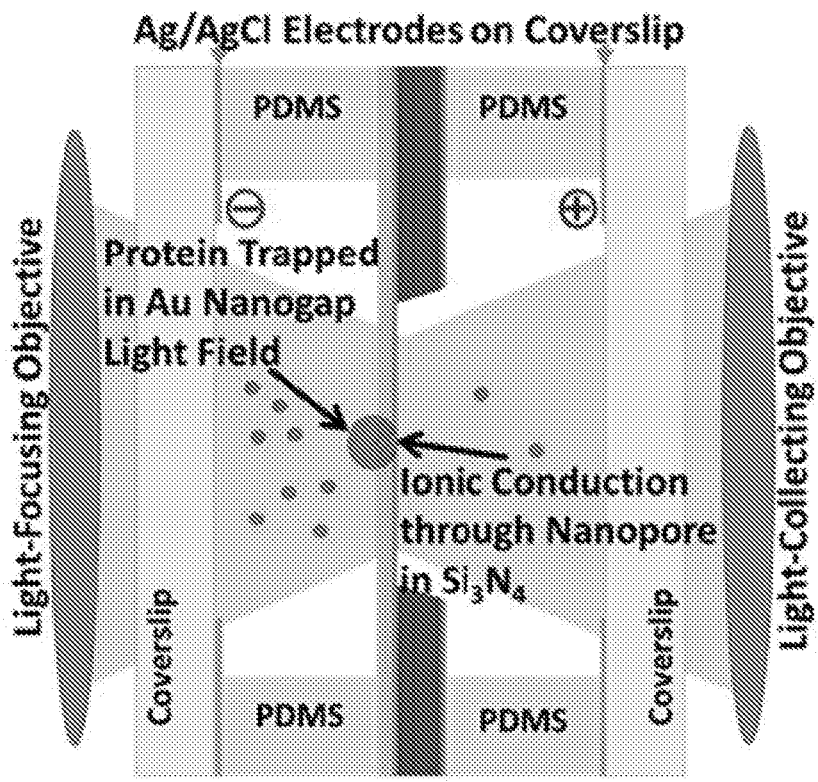
FIG. 4 schematically illustrates a dual electrical-optical sensor according to one embodiment described herein.
Figure 5:
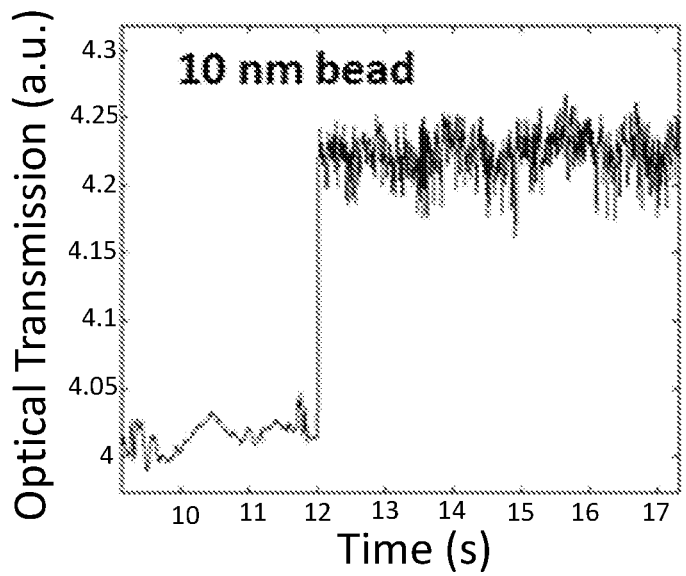
FIG. 5 illustrates an example measurement of a 10 nm bead trapping in a sensor.
Figure 6:
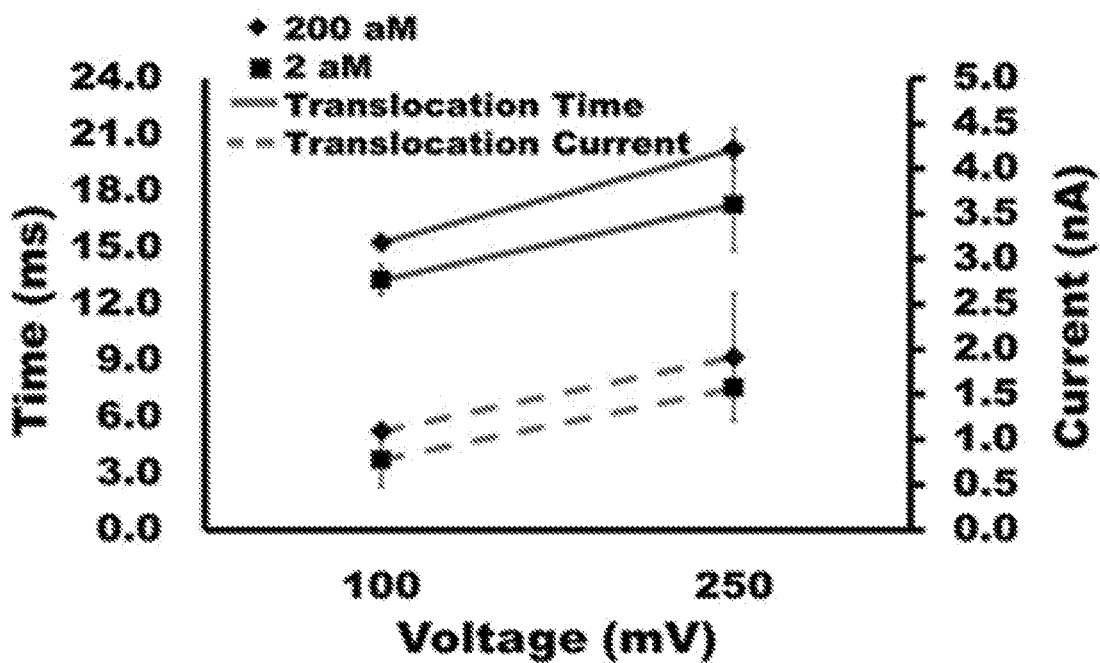
FIG. 6 is a graph of nanosensor translocation times and translocation current for 20 nm beads at 2 and 20 attomolar (aM).

The optical sensing setup and the electrical sensing setup are herein provided (FIG. 5). The electrical sensor does not occlude the beam path for optical measurements. Electrodes are deposited on both glass coverslips sandwiching the nanosensor so that nanobeads are pulled from solution by a voltage bias while focused light maintains optical trapping (FIG. 4). A micropump controls the inflow and wash-out of solutions through a PDMS chamber. The bimodal sensor presents a combination of competing forces that can be further selected as needed in given instance. Described herein are the range of light powers and voltage bias values for which a nanobead is trapped stably over the nanopore. As an example, EGFR proteins are nearly-globular with 10-14 nm diameter range. Further described are the estimated size of optical forces on spherical nanobeads in this size range using the product of optical polarizability to the average light intensity in the optical trap, which gives a trapping force of up to ~100 pN for typical excitation powers of a few mW. On the other hand, a typical voltage bias applied across the nanopore is 120 mV and at physiological pH (KCl 80 mM) EGFR has a net charge of up to 24e. For the case of nanobeads the pH of the solution can be adjusted so that the zeta potential of nanobeads corresponds to this effective charge value. The provided parameters result in a net electric field force on the nanobead of up to ~15 pN. These estimates were using methods for computing the electrophoretic force through a nanopore, which is reduced by counter-ion condensation and a small viscous drag factor. These estimates show that the net electrophoretic force is much smaller than the optical trapping force for typical experimental parameters. Furthermore, it is optional to reduce the voltage bias significantly, without compromising the electrical sensing capacity, to balance the competing forces. However, reduction of the voltage bias can result in significant noise, and degraded electrical sensing capability. Therefore, additional signal processing may be needed. Further provided herein are optical forces from FDTD calculations compared with COMSOL calculations for the electrical field force. Furthermore, changes in the voltage bias are used to estimate optical trap stiffness. Advantages of the optical-electrical sensor include: (1) Allowing active pulling of molecules from solution. This eliminates the need to wait for diffusion into the optical traps, thus greatly reducing dead time between trapping events. Moreover, this enables concentrations in the pM range compared to the hundreds of µM range; and (2) Detection of pore clogging and the ability to unclog it in real time by voltage bias reversal. Clogging of a pore by aggregates creates large reductions in both optical and electrical signal amplitudes. To avoid clogging, a logic circuit uses input signals from both the optical and electrical sensors to detect clogging events. Parameters of this logic circuit can be further selected to create on-the-fly rejection of aggregate settling over the pore through repulsion by electric field reversal immediately after detection.

Characterization of the Bimodal Sensor Sensitivity with In Vitro Pure Protein Solutions:

Methods described herein use a calibrated protein size kit spanning 5-500 kDa (GE28-4038-41, Sigma Aldrich) to measure mass and effective charge with each modality alone. The individual modality measurements are compared to the dual optical-electrical modality measurements. Effective charge is varied for each protein by changing the solution pH to vary the zeta potentials according to the manufacturer's specifications.

The sensitivity of the optical components are characterized based on the following considerations: optical sensing using the calibration shows that the combined sensor can detect protein sizes down to ~2.5 nm diameter. It is understood that data acquisition duration, limited by slow stage drift that leads to optical signal drift, impacts mass measurement accuracy. Statistical comparisons of fluctuation amplitudes with and without a trapped protein place the mass measurement limit at ~1 kDa.

The sensitivity of the electrical components are characterized based on the following considerations: electrical sensor geometry can be further selected to keep nanopore size and solution pH constant to study effective charge uncertainty and its dependence on mass measurement uncertainty. The calculations estimate a charge uncertainty of ~1e. This level of accuracy is shown in non-polar solutions with a micron-scale optical-electrical sensor.

Rejection of non-binding multi-protein trapping events: Described herein is the modulation of the optical trap intensity at frequencies matching the transit time of proteins across the trap. The detected signal fluctuations from both modalities indicate if more than one protein complex is in the trap. Non-bound proteins are verified by turning off the diode, forcing protein translocation through the pore. The laser diode has very fast response, below 1 µs, which is smaller than the ~5 us uncertainty of transit time measurement through the nanopore.

Described herein are methods of dual optical-electrical measurements to quantify the bound fraction of EGFR targeted by an RNA aptamer, and a mutant aptamer that does not bind EGFR. Also described herein are optical-only measurements for trapped EGFR-aptamer complexes. EGFR is ~175 kDa and the aptamers ~100 kDa; therefore, the two are distinguishable with the system's ~1 kDa sensitivity, which enables measuring the bound fraction by accumulating data from successive single complex measurements. The dual optical-electrical measurement allows testing on a complex-by-complex basis, regardless of whether each modality recognizes that there is a binding event or not. Described herein are tests of the accuracy that an association exists between categorical data from the two sensing modalities ("bound" versus "unbound" EGFR or aptamer) using a chi-square independence test. The pH of the solution is kept at a physiological 7.4, which is far away from the isoelectric point of the proteins used in this work. Therefore a non-zero effective charge exists around the proteins, which enables the electric field to pull proteins out of solution and into the optical trap. Once a measurement is completed the current is reduced on the laser diode to weaken the optical trap strength so that the protein complex can continue translocation through the nanopore. Paired t-tests are used to determine whether the combined sensor detects mass and effective charge with measurement uncertainties that are statistically distinguishable from corresponding measurements done with each modality alone. The results provide similar mass uncertainties, but improved effective charge uncertainties with the combined modality, as in the latter case, protein complex mass is measured and not assumed for each trapping event. Further provided is more electrical noise averaging with the bi-modal sensor as measurements last up to a hundred seconds, compared to few hundred us for electrical-only sensors that cannot slow down translocation through the nanopore. In this model no tyrosine kinase inhibitor is used as it is difficult to recapitulate the EGFR phosphorylation conditions in pure protein solution with commercially available reagents.

Detecting Changes to Protein Complex Formation in the Presence of Inhibitor for EGFR Isolated from Cell Lysate.

First EGFR is isolated from cell lysate of WT and mutant-expressing cell lines and the bound fraction of phospho-antibodies targeting EGFR are quantified using the optical-electrical nanosensor. The EGF-induced EGFR phosphorylation of Tyr1173 in A549 (WT, ATCC) and PC9 (mutant, Sigma-Aldrich) cell lines is verified in whole cell lysate with ELISA readout using an appropriate kit (Millipore, 17-461). IP of EGFR overexpressed in these cell lines is performed with a polyclonal anti-EGFR antibody (Millipore, 06-847), using EGF-stimulated A431 cell lysate as positive control (Millipore, 12-302). This antibody is validated for IP and produces a clear single EGFR band in western blots. The EGFR eluted from the pull-down is mixed with a specific phospho-antibody targeting Tyr1173 (Millipore, 16-244). The bound fraction of the phospho-antibody to EGFR in any one set of experimental conditions is quantified by accumulating data on the mass and effective charge of the protein complex trapped at the nanosensor. After acquiring data for a single protein complex for durations enabling maximum measurement accuracy, the complex is pushed through the nanopore by transient reduction of the optical trap power and then another complex is attracted from solution. The accumulation of sequential observations where EGFR is detected alone or bound to the anti-EGFR antibody, as judged from its mass-change optical-electrical measurements, allows calculation of the bound fraction for each experimental condition.

Subsequently quantified is the change in phospho-antibody fraction bound to EGFR isolated from cells exposed to a specific phosphorylation inhibitor using the bimodal sensor. To that end, Gefitinib inhibitor that targets Tyr1173 and other residues (Selleckchem, ZD-1839) is added in each cell line before pulling down EGFR from the lysate. Both of the A549 and PC9 cell lines are very sensitive to this inhibitor with IC50 values of 1 nM and 4 nM, respectively. These are the target inhibitor concentrations initially which can be subsequently adjusted. Antibodies designed to bind to the same phosphorylation site that this inhibitor targets are added (Anti-phospho-EGFR for Tyr1173, 16-244, Millipore) and the bound anti-EGFR fraction for receptors is quantified from both cell lines. The change in bound fraction with respect to the same experiments performed previously is calculated without addition of the inhibitor and paired t-tests are used to identify significant differences. In some instances a mixed population of WT and mutant receptors is pulled from the lysate by the polyclonal anti-EGFR; therefore, additional measurements with an antibody that targets the non-phosphorylated Tyr1173 (Millipore, 05-484) are performed. The latter experiments quantify the fraction of EGFR not phosphorylated in the absence and presence of inhibitor, which can be used to correct the bound fraction calculations. As a final validation step the phospho-antibody binding inhibition by Gefitinib is quantified by LC-ESI-MS/MS or MALDI-TOF MS after the protein complex solutions are measured with the nanosensor.

Example 3

The present example reports nanofabrication and proof of principle studies for a DNH-ssNP sensor enabling simultaneous self-induced back action (SIBA)-mediated optical trapping by the DNH and electrophoresis through the ssNP. The present sensor is described as a SIBA Actuated Nanopore Electrophoresis (SANE) sensor. The nanopore is milled between the tips of the DNH where the highest plasmonic energy is focused, resulting in trapping of the nanoparticle due to dielectric loading at the mouth of the nanopore. The nanoparticle translocates through the nanopore after it escapes trapping and yields the characteristic drop in ionic current due to pore blockage. Two types of focused ion beam (FIB) milling enabled nanofabrication of the DNH structure in an Au layer deposited on top of a thin silicon nitride layer without damaging it. Furthermore, the DNH structure is known to dissipate heat very effectively with minimal temperature increases at optical trapping powers. In proof of principle experiments, the DNH-nanopore structure trapped 20 nm nanoparticles made of silica or Au for several seconds, while enabling their concurrent electrical sensing during the same time interval. The SANE sensor controlled the nanoparticle translocation through the nanopore, which extended the duration of electrical sensing by up to four orders of magnitude compared to nanopore sensing alone. The extended electrical measurement times revealed a newly observed high frequency charge transient phenomenon related to occupancy of the optical trap by one or more nanoparticles. Finally, we discuss how upon sensor calibration, these bimodal measurements could be used to estimate the total charge around a nanoparticle and how SANE sensor measurements characteristics differ between silica and Au nanoparticles due to differences in their physical properties.

Dual Nanohole—Nanopore Chip Fabrication

The fabrication was done on double side polished, (100) orientation 4-inch silicon wafer. Wet thermal oxidation was done to grow 500-1,000 nm $SiO_2$ on both sides of the polished wafer followed by deposition 60-70 nm of either stoichiometric or non-stoichiometric low stress silicon nitride ($Si_xN_y$) by low pressure chemical vapor deposition (LPCVD). For each wafer, individual 15 mm×15 mm square chips were created with one side patterned using S1813 photoresist with a dark field backside mask. The first mask contained square windows of 786 μm size in the center. The 786 μm square etch windows were opened in $Si_xN_y$ using $CF_4$ plasma deep reactive-ion etching (DRIE) for 100 seconds to etch through its entire 60 nm layer thickness and then a 6:1 Buffered Hydrofluoric acid (BHF) solution was used to etch the $SiO_2$ to reveal the bare silicon (FIG. 7).

The wafers were placed in 22% tetramethylammonium hydroxide (TMAH) solution at 90° C. to anisotropically etch the wafer all the way to the front side revealing the 100 μm square $SiO_2/Si_xN_y$ membranes at the other side, henceforth called the front side. The $SiO_2$ was a sacrificial layer to protect the membrane during further processing and was etched away at the last step of the chip fabrication. The wafers were cleaned in Piranha solution and inspected under an optical microscope to confirm the design parameters of the anisotropic etch. E-beam evaporation was used to deposit 5 nm of Cr as the adhesion layer at a rate of 0.5 Å/sec on which 100 nm of Au was subsequently deposited at a rate of 1 Å/sec on the front side of the wafer on top of the suspended $Si_xN_y$ membranes. The S1813 positive resist was used to coat the front side of the wafer to pattern four diagonal FIB alignment markers in Au. A backside aligner (EVG 620) was used to align the dark field second mask and to expose the front side while aligned to the backside patterns. Au and Cr were wet etched using commercially available wet etchants (Sigma Aldrich). The etched and cleaned wafers were inspected under an optical microscope for proper placement of FIB alignment markers on the suspended $Si_xN_y$ membrane from the front side and the back side (FIG. 7D). The front side of the wafers was coated in thick S1813 photoresist and hard baked. The individual chips were diced and separated from each other. The sacrificial $SiO_2$ layer beneath the $Si_xN_y$ was then wet etched from the back side using 6:1 BHF for 8 min and the photoresist layer on the front side was removed in acetone. The individual chips were dried and inspected under an optical microscope to confirm the integrity of the membrane and of the alignment markers on it. The membrane area now consisted of a 50 nm thick $Si_xN_y$ layer with a 5 nm Cr/100 nm Au metal stack (FIG. 7C). These 15 mm×15 mm individual chips were now ready for FIB milling (FIG. 7D).

The FIB milling on these individual chips was done using a mix of Ne and He GFIS focused ion beams (Carl Zeiss, ORION NanoFab, Peabody, MA). In the present instance, a Ga FIB or TEM beam was not used due to the complex requirements of the dual layer design (FIG. 7C). The dumbbell shape of the DNH was milled into the Au film (Critical Dimension=25 nm) and the milling had to be stopped at the metal/dielectric interface. The DNH shape was designed to have 15-20% tapered edges (FIG. 7F), converging towards the metal/dielectric interface. A Ne ion beam was used to mill the DNH shape in the Au/Cr metal stack (500 fA beam current, 25 kV acceleration voltage, 10 μm aperture and 8.5 mm working distance). A beam dose of 0.2-0.225 $nC/\mu m^2$ was determined to be suitable to reach the Au/Cr—$Si_xN_y$ interface. The secondary electron current was used in the nanopatterning visualization engine to determine when the dielectric interface was reached to terminate the Ne FIB milling. At that point, the beam was switched to He ions and a 25 nm circle was drilled through the suspended $Si_xN_y$ membrane in the middle of the DNH shape (2 pA beam current, 30 kV acceleration voltage with 150 $nC/\mu m^2$ dose, 10 μm aperture and 8.5 mm working distance). He FIB nanopore drilling through the $Si_xN_y$ film was stopped when the secondary electron current suddenly decreased to almost zero (FIG. 7E).

Experimental Setup

The beam from an 820 nm laser diode (L820P200, Thorlabs) was collimated to a 2 mm diameter and circularly polarized through a QWP (WPQ05M, Thorlab), followed by a Glan-Thompson linear polarizer (GTH10M, Thorlabs) for controlling the polarization of light incident on the chip. The light then passed through a tunable HWP (WPH05M, Thorlabs) to make the direction of polarization perpendicular to the DNH's long axis to excite maximally wedge plasmons for trapping. A downstream 4× beam expander (Newport) was used in combination with an 8 mm circular aperture (ID.1.0, Newport) to make the intensity profile of the cylindrical beam flatter. The beam then went through a periscope and into the back aperture of a 63× oil immersion objective lens and focused onto the front Au side of the SANE chip. The objective's focal spot was aligned with the DNH center by adjusting the piezoelectric stage controls until polarized light transmission was maximized. Light transmission through the FIB alignment markers was used as a first coarse step to find the DNH on the chip. The light transmitted through the chip's center and any leakage light scattering through alignment markers was collected by a condenser lens and focused onto a photodiode (PDA36A, Thorlabs) (FIG. 8).

Figure 8A:
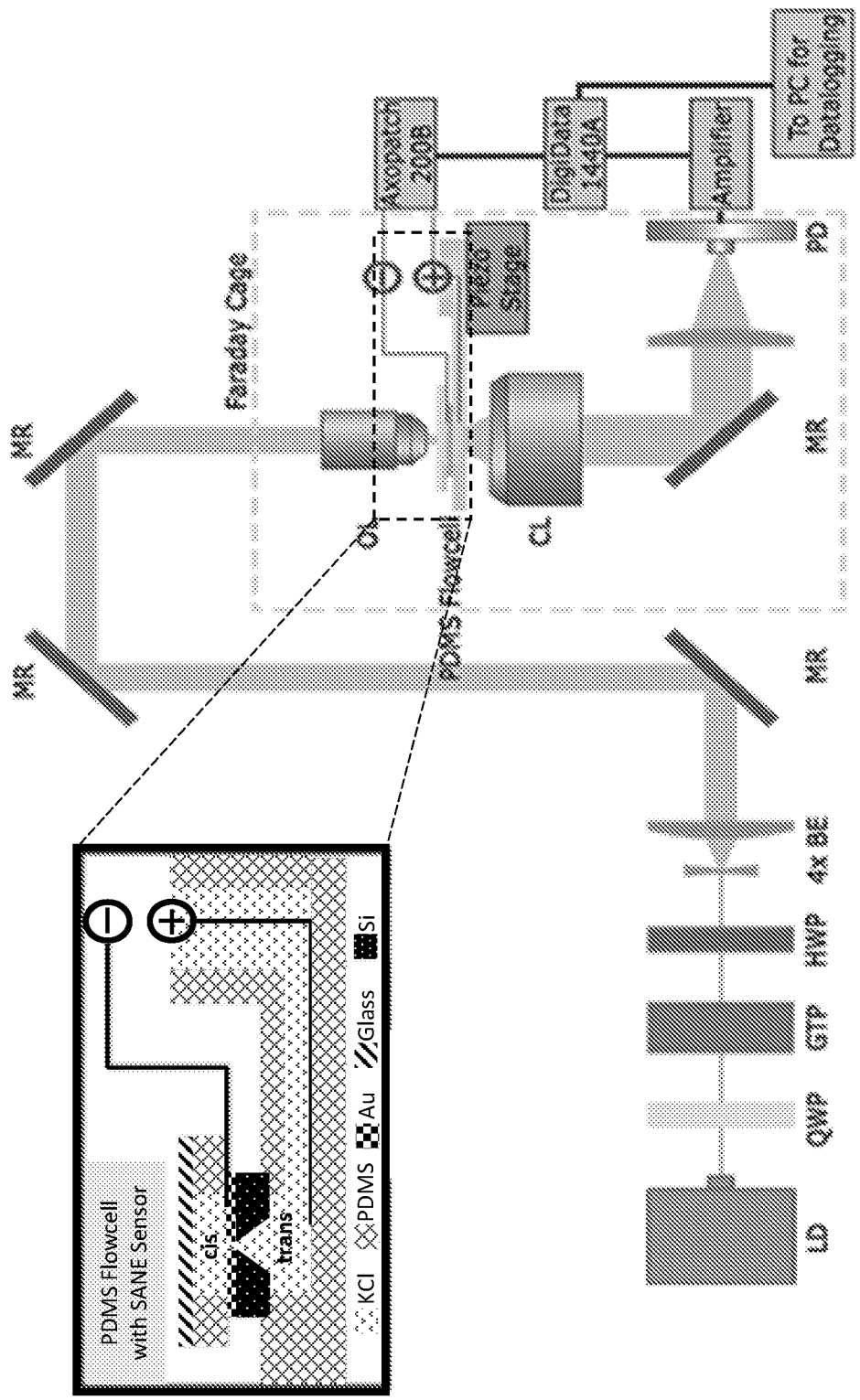
FIG. 8A is a schematic of a complete optical setup with PDMS flow cell placement and measurement instruments. An exploded cross-sectional view of the PDMS flow cell with a sensor is also provided. LD: Laser Diode, QWP: Quarter Wave Plate, GTP: Glan-Thompson Polarizer, HWP: Half Wave Plate, 4×BE: 4× Beam Expander, MR: Mirror, OL: Carl-Zeiss 1.3 N.A. 63× Objective Lens, CL: Condenser Lens, PD: Photodiode.
Figure 8B:
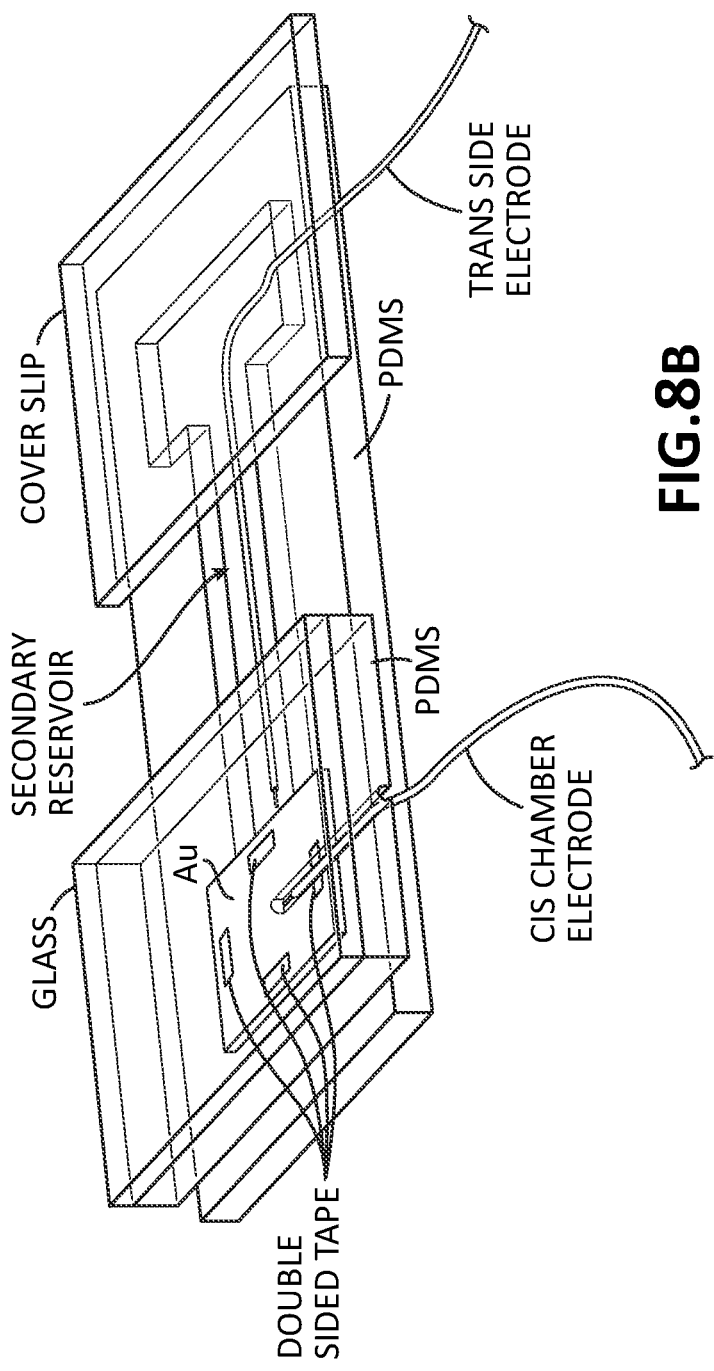
FIG. 8B is a photograph of a prepared PDMS flow cell with a sensor chip, as described herein, ready for placement on a piezo-controlled stage.

Standard soft lithography techniques were used for fabrication of a flow cell that could house the SANE sensor chip with a cis and a trans chamber for the nanopore and to provide optical access to the DNH. The flow cell was made from polydimethylsiloxane (PDMS) mixed in a 10:1 ratio of polymer to initiator as prescribed by the manufacturer (Dow Corning). This mixture was degassed to remove air bubbles and subsequent fabrication was performed in three steps. In the first step, a flat PDMS slab of 1-3 mm thickness was created by adding the bubble-free mixture to a cavity created on a polished side of a silicon wafer and curing it on a hotplate at 100° C. for 10 min. After peeling this PDMS slab, a pattern was cut into it consisting of a 10 mm square opening at the center and a 2 mm wide rectangular channel connecting it to another 10 mm square opening towards the end of the slab (FIG. 8A). The PDMS slab was bonded onto a 3 in×2 in glass slide using oxygen plasma (Electro-Technic). In the second step, the SANE sensor was placed over the central square opening using a double-sided tape (3M) sealing the square opening underneath and creating the trans chamber of the nanopore. Another flat PDMS slab of 3 mm thickness was created using the same procedure and a hollow rectangle was cut and placed over the square opening at the end of the slab using double-sided tape (FIG. 8B). This secondary chamber acted as a reservoir holding enough ionic solution to keep the bottom of the nanopore always wet. The rectangular channel connecting these openings was also covered with the same double-sided tape to completely seal the flow path. In the third step, a 1-inch coverslip of 170 μm thickness (VWR) was plasma-bonded onto a very thin PDMS layer of 200 μm thickness, with a square opening of 10 mm cut through the center of this layer to form a cis chamber over the SANE sensor. An additional 1 mm wide gap was cut at the edge of this PDMS layer to allow introduction of analyte into the cis chamber along with the cis chamber electrode. Subsequently, the trans side was gently filled with ionic solution using Teflon tubing connected to a syringe up to the brim of the 3 mm PDMS reservoir wall. To complete the electrical path, the trans side electrode was introduced through the reservoir wall and pushed along the rectangular channel until its tip was located right below the sensor. Finally, the secondary reservoir was topped with a coverslip to confine the ionic solution within the flow cell. This flow cell was attached to a holder and the assembly was screwed onto a piezo-controlled translation stage (MDT6938, Thorlabs) immediately below the objective lens. The prepared PDMS flow cell with the SANE chip is shown in FIG. 8B.

To implement electrical sensing the cis and trans chamber Ag/AgCl electrodes were attached to the Axon Headstage (CV 203BU) of the Axon Axopatch 200B patch clamp in voltage clamp mode. A custom-made Faraday cage using copper wire mesh (PSY405, Thorlabs) was installed to cover the entire optical assembly and shield the PDMS flow cell from low-frequency electromagnetic noise during highly sensitive patch clamp ionic current recordings.

Subsequently, the nanopore was first tested for wetting. If the nanopore was blocked, an alternating ±5 volts square wave was applied to the two electrodes for 60 sec to unblock the nanopore through electrophoretic pressure. After wetting, the trans side reservoir of the PDMS flow cell was filled with 7.4 pH 1M KCl solution and the cis reservoir was filled with 200 pM solution of 20±4 nm silica nanoparticles (MEL0010, NanoComposix, zeta potential=−40 mV) suspended in the same solution. Au nanoparticles (C11-20-TM-DIH-50, Nanopartz, zeta potential=−15 mV) of the same size and concentration as silica were also used to fill the cis reservoir in separate experiments. A 2 nm thick methyl polymer coating on the Au nanoparticles helped maintain their stability in KCl solution. The PDMS flow cell was attached to the piezo-controlled stage using screws and the laser beam was aligned to the DNH center as described above. A 250 mV bias was applied through the patch clamp in voltage clamp mode. The photodiode and Axopatch 200B signals were both sent through an Axon Digidata 1440 ADC to a PC for recording and data analysis in Axon Clampfit 10.6 software. The complete experimental setup schematic is shown in FIG. 8A. In subsequent data analyses, the coefficient of variation was defined as the ratio of standard deviation to the signal mean value and the ionic current translocation time and signal to noise ratio (SNR) during translocation were defined as described previously.

Results

Figure 9:
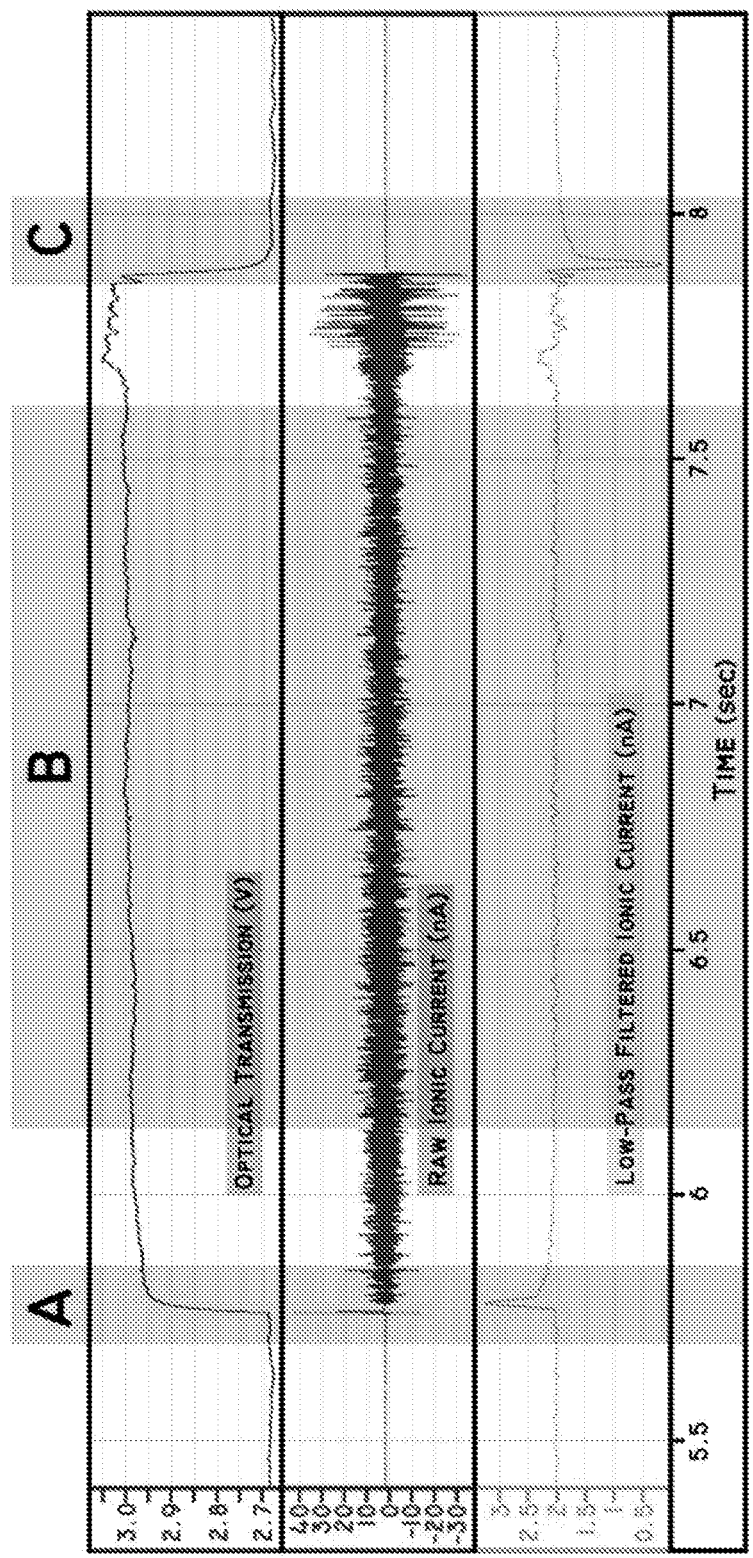
FIG. 9 is a plot of simultaneously recorded optical transmission (top panel), raw ionic current (middle panel), and 20 Hz low-pass filtered ionic current (bottom panel) versus time (sec) for a single 20 nm silica nanoparticle trapped in a sensor described herein. Regions A, B, and C represent particle entry, trapping, and exit, respectively.

FIG. 9 shows the first proof of principle measurements with the SANE sensor that demonstrate multi-second trapping of a single 20 nm silica nanoparticle with concurrent electrophoretic measurements through the nanopore at the center of the DNH. When the 20 nm nanoparticle was trapped by the DNH, a step increase of 11% in optical transmission was seen due to dielectric loading of the trap (FIG. 9). Concurrently, high frequency transients were seen in the raw ionic current (FIG. 9), registering a positive charge peak of ~38 nA which was 19 times higher than the baseline nanopore current. These ionic current oscillations were likely caused by axial nanoparticle oscillations, which we will henceforth refer to as 'bobbing', in the nanopore vicinity due to opposing optical and electrical forces. It is noteworthy that optical trapping enabled ionic current sensing of the nanoparticle for a few seconds, which is about four orders of magnitude longer than the typical current sensing times for nanoparticle translocation events through a nanopore alone.

Figure 10C:
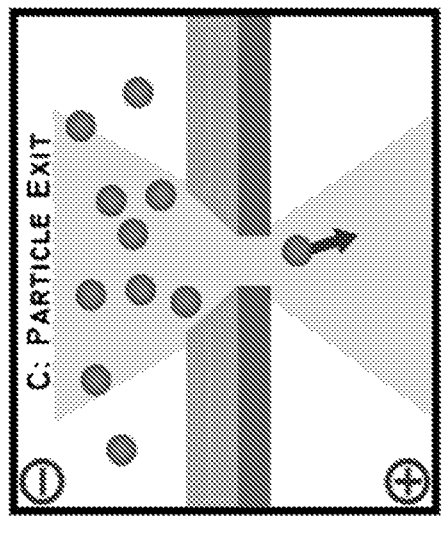
FIG. 10C is a schematic illustrating the physical interpretation of the signal recorded in Region C of FIG. 9, wherein a nanoparticle is exiting the optical trap after the electrophoretic force dominates translocation.
Figure 10B:
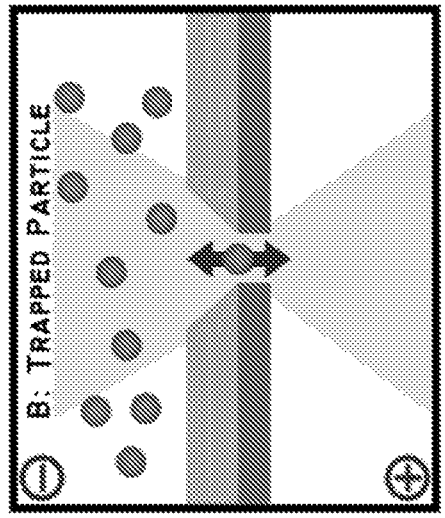
FIG. 10B is a schematic illustrating the physical interpretation of the signal recorded in Region B of FIG. 9, wherein a nanoparticle is trapped and bobbing inside the DNH near the ssNP mouth.
Figure 10A:
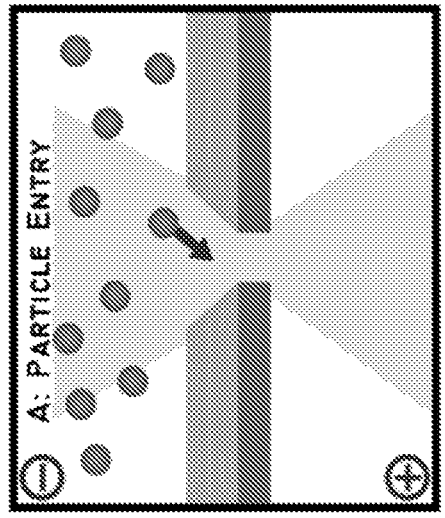
FIG. 10A is a schematic illustrating the physical interpretation of the signal recorded in Region A of FIG. 9, wherein a negatively charged nanoparticle is entering the dual nanohole-solid state nanopore (DNH-ssNP) under applied bias.

The recorded raw ionic current was also filtered with a 20 Hz, low pass 8-pole Bessel filter in Axon Clampfit 10.6 to enable visualization of the nanoparticle movement effects on low frequency ionic current. A distinct positive peak of 26.2 ms was registered during charged nanoparticle entry in the DNH, when the trapping started (FIG. 9, Region A and FIG. 10A). The nanoparticle was bobbing inside the DNH trap for about 2.15 sec (FIG. 9, Region B and FIG. 10B) and the low-pass filtered ionic signal did not show any appreciable changes during that time. Towards the end of the trapping period, the amplitude of high frequency transients increased concurrently with a slight increase in optical transmission before the nanoparticle escaped and translocated through the nanopore [FIG. 9, Region C and FIG. 10C]. When the nanoparticle translocated across the ssNP from the cis to the trans region, a characteristic negative ionic current pulse was seen (third row, green) due to nanopore blockage during translocation (1.79 nA, translocation time 22.3 ms) taking place concurrently with a drop in optical transmission decrease back to the baseline (first row, blue).

Figure 11:
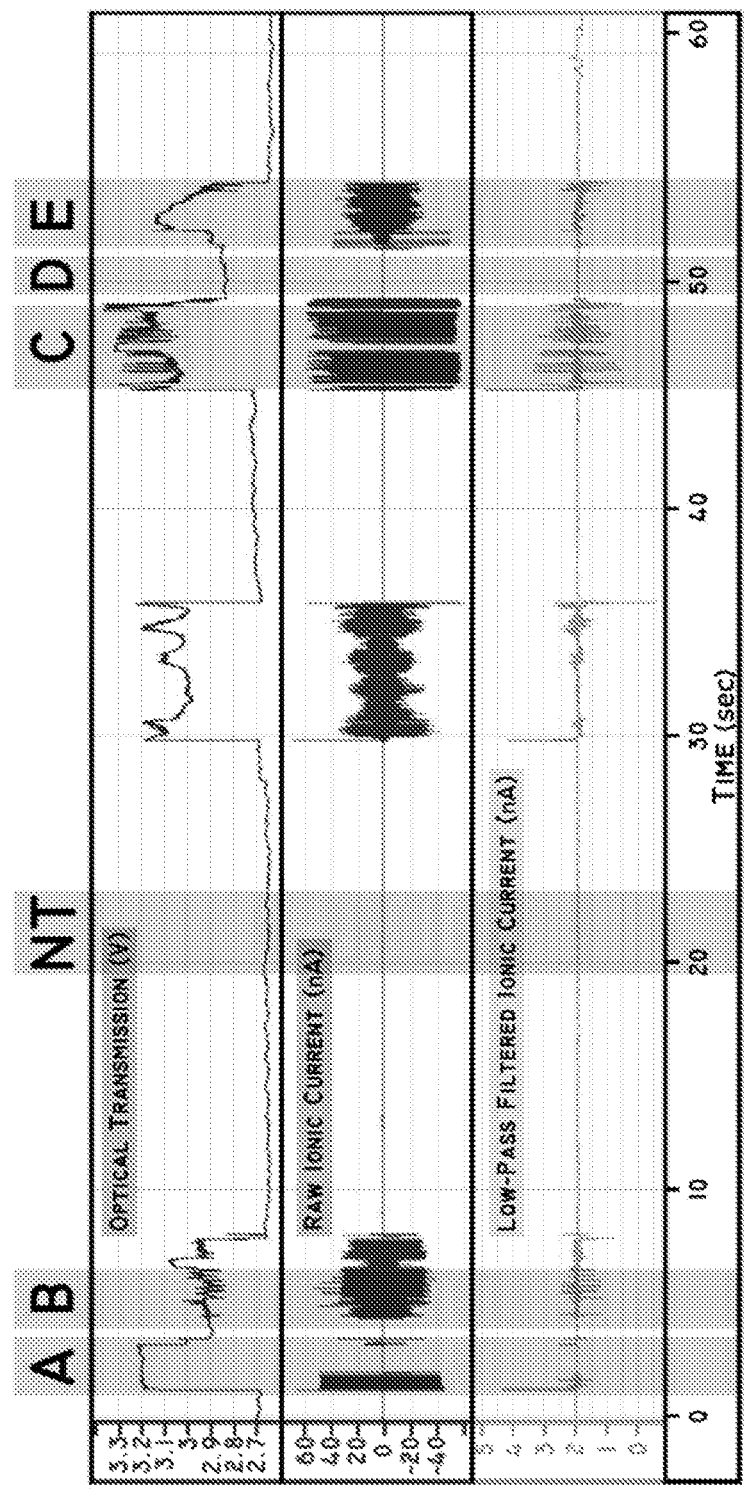
FIG. 11 is a plot of simultaneously recorded optical transmission (top panel), raw ionic current (middle panel) and 20 Hz low-pass filtered ionic current (bottom panel) versus time (sec) for a 1 min trace with three complex multi-particle trapping events.
Figure 12A:
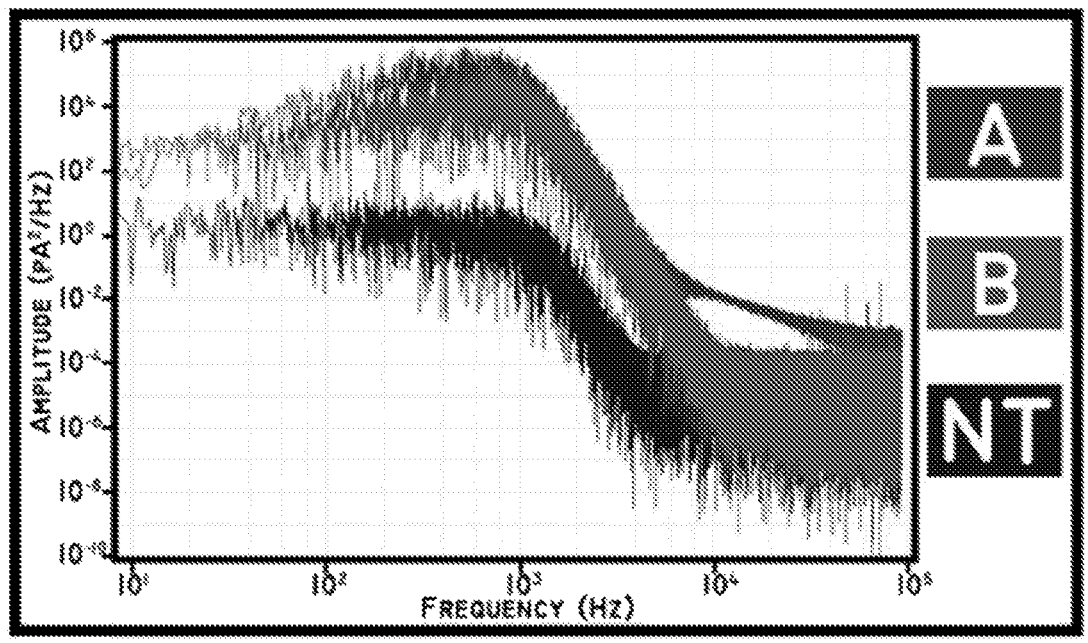
FIG. 12A is a power spectrum analysis of the raw ionic current signal for Regions A, B and a No-Trapping (NT) region of FIG. 11.
Figure 12B:
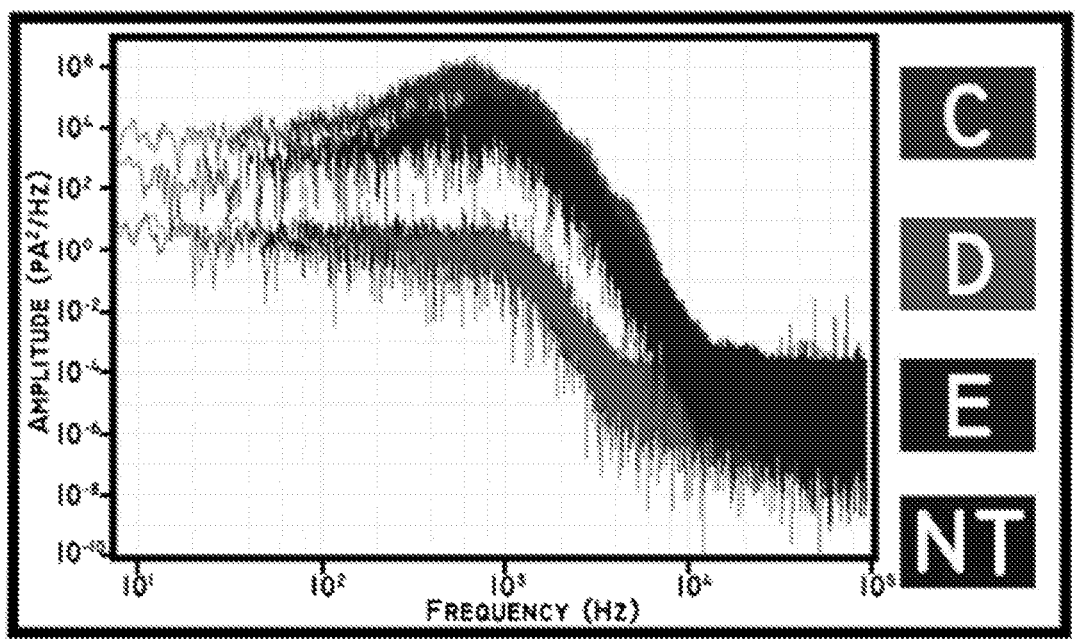
FIG. 12B is a power spectrum analysis of raw ionic current signal for Regions C, D, and E, including NT for reference, which is largely masked by Region D.

In addition to single trapping events, more complex multiple nanoparticle trapping events were recorded and analyzed as well. FIG. 11 provides a 1 min trace showing three such trapping events. The gray-shaded Region A in that figure highlights a two-nanoparticle trapping event, as deduced from the nearly doubled optical transmission amplitude compared to the trapping event in Region B (10±2% versus 18.5±1%). Frequency spectrum analysis of raw ionic current signals for Regions A and B is shown in FIG. 12A. Interestingly, the peak of the frequency spectrum for Region A was found in the 850 Hz range whereas it was in the 1 kHz range for Region B. The latter had a remarkably similar power spectrum for the single nanoparticle trapping event described in FIG. 9 (frequency spectrum not shown for brevity). Furthermore, the frequency spectrum from a No-Trapping (NT) period is included for comparison in FIG. 12A, demonstrating a plateau rather than a peak frequency and spectral amplitudes that were up to four orders of magnitude lower than those for trapping events. These spectral differences suggest the ability of differentiating single versus double nanoparticle trapping events over background signals with the SANE sensor. A representative sequence of multiple nanoparticle trapping events is highlighted in Regions C and D of FIG. 11. FIG. 12B shows the power spectra of these Regions and compares them to the NT condition. The power spectrum of Region C with an amplitude peak at 850 Hz and a 19.5±1% increase in optical transmission shows a two-nanoparticle trapping event. Optical transmission in region D was 8.7±1% over baseline, indicating single nanoparticle trapping. However, the raw ionic current showed no high frequency transients in Region D, making its frequency spectrum indistinguishable from the NT condition, even though optical transmission indicated single nanoparticle trapping. Not intending to be bound by theory, it is believed that during this period the nanoparticle attained transient equilibrium in the DNH-ssNP trap and was not bobbing significantly. In Region E, another nanoparticle entered the trapping site, indicated by an increase in optical transmission to 15±1% and shifted the ionic current fluctuation spectral peak from ~1 kHz to ~900 Hz. These observations are interpreted as the entry of an additional nanoparticle instigating bobbing for both nanoparticles inside the trap before these translocated through the nanopore.

Figure 13:
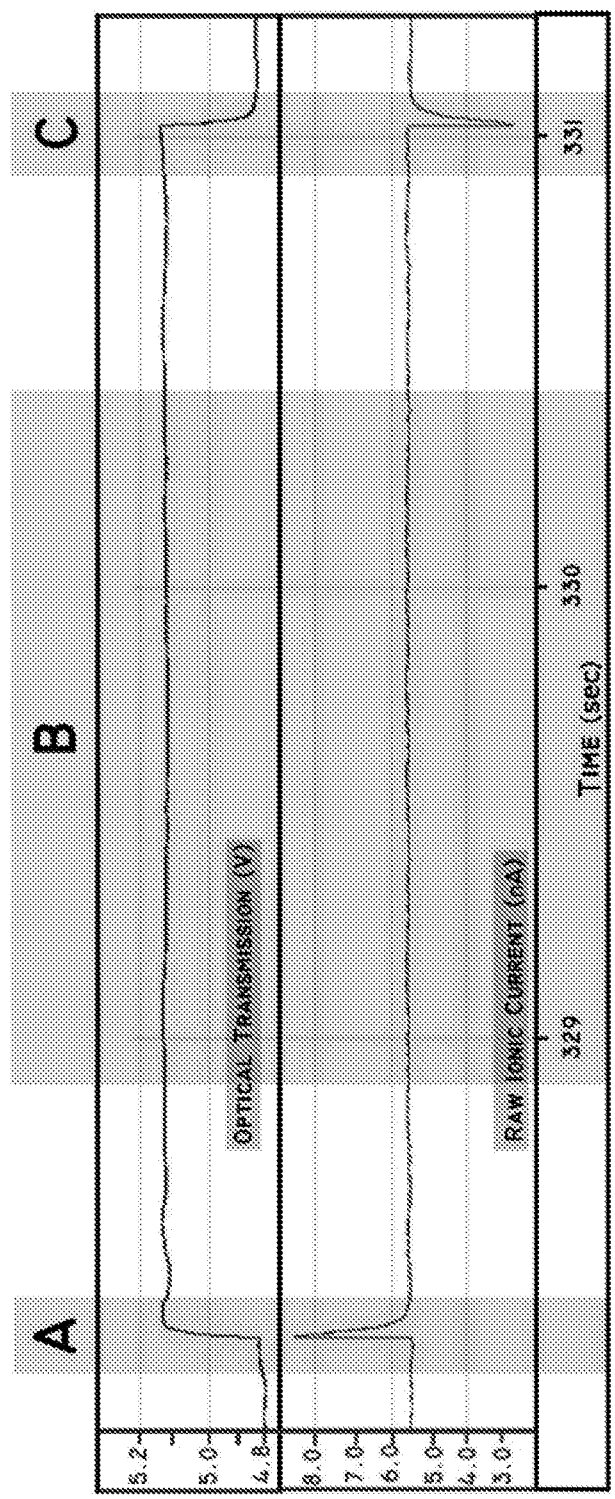
FIG. 13 is a plot of simultaneously recorded optical transmission (top panel) and raw ionic current (bottom panel) versus time (sec) for a single 20 nm Au nanoparticle trapped in a sensor described herein. Region A: Au nanoparticle entering the DNH-ssNP under applied bias. Region B: Nanoparticle trapped inside the DNH near the ssNP mouth. Region C: Nanoparticle exiting the optical trap after the electrophoretic force dominates translocation.

To further investigate the influence of charge of individually trapped nanoparticles on SANE sensor measurements, 20 nm methyl functionalized Au nanoparticles were also measured under identical experimental conditions to the silica ones, so as to make comparisons. FIG. 13 shows the trapping event and electrophoretic movement of a single Au nanoparticle. When the nanoparticle was pushed towards the DNH center by the electrophoretic force, its optical trapping caused a rise in optical transmission of ~6%. Simultaneously, the raw ionic current through the nanopore registered a positive peak of ~8.5 nA for 27 ms, as the particle entered the trap [FIG. 13, Region A]. Unlike the silica nanoparticles, the electrical high frequency transients during particle trapping were attenuated to very low levels. At the same time, the coefficient of variation of optical fluctuations during Au nanoparticle trapping reduced to ~0.02% compared to the ~0.11% seen for the silica nanoparticle fluctuations [FIG. 9, Region B]. Typical Au nanoparticle trapping durations were a few seconds, 3.28 sec in [FIG. 13, Region B]. Subsequently they escaped trapping and translocated through the nanopore [FIG. 13, Region C]. A negative ionic current pulse was measured during translocation, while the Au nanoparticle blocked the nanopore (2.64 nA, translocation time 19.1 ms). At the same time the optical transmission dropped back to the baseline.

Comparisons of SANE sensor measurement characteristics for Au versus silica nanoparticles highlighted a number of differences: (1) Au nanoparticles had a lower optical step increase from baseline compared to silica by a factor of 2.9±0.4 (2) The coefficient of variation for the optical signal during trapping was lower than silica by a factor of 148.3±2.4. (3) After applying the same 20 Hz low pass 8-pole Bessel filtering to the ionic current during Au nanoparticle optical trapping, the coefficient of variation was lower than silica by a factor of 5.5±1.2. (4) Translocation times were slower for Au nanoparticles by a factor of 0.87±0.05. (5) The ionic current during Au nanoparticle translocation was higher than silica nanoparticles by a factor of 1.7±0.3, resulting in an SNR of ~72 compared to ~43 for silica. These differences are considered in the Discussion section below.

Discussion

In the present study, the nanoparticle translocation dynamics changed drastically due the SIBA-actuated trapping of the nanoparticle in the DNH nanocavity. The trapping force acting on the nanoparticle remained balanced for several seconds, e.g. 2.15 sec for the particle shown in FIG. 9. Furthermore, the characteristic negative peak due to ionic current blockage lasted 58.876 ms for the single 20 nm nanoparticle translocation event shown in FIG. 10C, which is much longer than the 200±30 µs translocation times of similar nanoparticles in nanopores. Therefore, optical trapping enabled ionic current recordings in the vicinity of the nanopore that were about four orders of magnitude longer than typical translocation times for similar nanoparticles and also slowed down their translocation through the nanopore.

The greatly extended ionic current recording times also revealed a newly observed high frequency charge transient phenomenon for silica nanoparticles. Not intending to be bound by theory, it is believed that this originates from bobbing of the nanoparticle through the mouth of the nanopore due to the competing electrophoretic and SIBA forces. These high frequency transients were seen both for single [FIG. 9] and multiple [FIG. 11] nanoparticle trapping. At the end of the single trapping event seen in FIG. 9 (Region D), the nanoparticle started bobbing, which resulted in larger amplitudes for both ionic current and optical transmission. These observations suggest that the electrophoretic force led the nanoparticle to translocate through the ssNP.

It was observed that the peak amplitude of high frequency transients for raw ionic current decreased as dielectric loading in the trap increased from a one (~1 kHz) to two (~850 Hz) silica nanoparticles. Therefore, frequency spectrum analysis of the SANE sensor's raw ionic current shows promise for distinguishing single nanoparticles from more complex trapping events. In addition to periods of high frequency ionic current transients, instances of trapping with relatively quiet ionic current signals were also observed. For example, the single nanoparticle trapping in FIG. 11 (Region D), with similar optical transmission amplitude as Region B did not show any high frequency transients. Again not intending to be bound by theory, it is believed that this behavior was a result of transient equilibrium while the single nanoparticle was blocking the pore and temporarily stopped bobbing. However, when another nanoparticle entered the DNH trap this equilibrium was disturbed and the high frequency charge transients returned with a peak frequency of ~900 Hz (Region E) in the raw ionic current trace [FIG. 12B]. The latter behavior was consistent with two-nanoparticle trapping. The subsequent gradual decrease in optical transmission and low-amplitude spikes in the low-passed ionic current in Region E suggest that the two nanoparticles translocated through the nanopore sequentially and not as a single unit. These findings indicate that the SANE sensor can provide information on the dynamics of single and two-nanoparticle dynamics inside the optical trap.

Experiments were performed subsequently with Au nanoparticles of the same size under identical experimental conditions to silica to compare the effect of nanoparticle charge on SANE measurements. The lower change in optical transmission compared to silica when Au nanoparticles entered the optical trap could be attributed to differences in optical interaction cross-sections. Although the scattering cross-section of 20 nm Au nanoparticles in water is ~59% higher than that of the silica ones at 820 nm, the absorption cross-section is about 4 times larger than scattering for the Au nanoparticles. In contrast, silica nanoparticles have negligible absorption. The reduced coefficient of variation in optical signal during Au nanoparticle trapping is therefore expected to be at least in part due to increased absorption. In addition, Au is a conductor and the applied voltage bias across the sensor would exert an electric field force on the Au nanoparticles, which would push towards a preferential direction in nanoparticle displacement that can constrain free diffusion. Indirect evidence for the existence of an electric field force was seen in the shorter translocation times of Au nanoparticles even though they had a lower zeta potential relative to the silica nanoparticles. In addition to the reduced translocation time, the observed increase in ionic current amplitude during translocation for Au nanoparticles is consistent with a zeta potential based interpretation and resulted in the observed increase in SNR compared to silica. Finally, it was evident that the raw ionic current during Au nanoparticle trapping [FIG. 13, bottom, red, Region B] had significantly reduced high frequency charge transients compared to silica. Although Au nanoparticles had reduced displacement amplitudes within the trap, as discussed above, the charge fluctuations around the nanoparticle can play a major role. Since Au is conducting, charges within the nanoparticle can move around to cancel out charge fluctuations in its immediate vicinity.

Finally, using calibrated SANE sensor measurements is contemplated to estimate the number of total surface charges around unknown analytes. The Grahame equation can be used to calculate total surface charge using the experimentally determined zeta potential of the analytes by the SANE sensor. The zeta potential can be deduced from the electrophoretic mobility of the analytes, which entails measurement of their translocation time and knowledge of the applied bias and nanopore size. Concurrent optical measurements of analyte radius can be used to determine which approximation of Smoluchowski's theory is appropriate for deducing the zeta potential. For experimental parameters relevant to this work the appropriate approximation is the Hückel equation, which would yield the zeta potential estimate for the analytes. These considerations indicate the ability of calibrating the SANE sensor's optical and ionic current signals to estimate the charge around unknown analytes by direct measurement of their radius and electrophoretic mobility.

Conclusions

The present example demonstrates multi-second optical trapping of electrophoretically translocating nanoparticles through a ssNP. The competing electrophoretic and SIBA forces induced bobbing inside the optical trap that led to high frequency ionic current oscillations sensed through the nanopore. Frequency analysis of these oscillations for silica nanoparticles demonstrated the ability of distinguishing between one versus two nanoparticles inside the trap. Furthermore, the SANE chip's bimodal sensing ability showcased its use as a tool to estimate the charge around a nanoparticle. Different SANE sensors were used to collect the measurements for this work which demonstrated the repeatability of this approach.

Example 4

In this example a sensor is designed to (1) operate at pM concentrations of peptide/MHC ligands enriched from only a few thousand cancer cells to significantly reduce the tumor biopsy needed and (2) identify aggregates and non-specific binding events and distinguish them from true binding events based on their bimodal optical and electrical sensor signatures. The sensor uses localized plasmon resonance coupled with an electrical sensing nanopore to 'arrest' dynamically individual complexes over the nanopore. Optical trapping prevents the protein complex from translocating quickly through the nanopore and enables simultaneous quantification of mass (optical signal) and effective charge (electrical signal). Experiments herein test whether mass and effective charge measurements performed with this sensor can identify specific peptide/MHC ligand-antibody complexes enriched from several cancer cell lines that knowingly express them as examples. These proof of principle experiments are intended to demonstrate the ability of this sensor to work with heterogeneous solutions at low protein concentrations. Enriched ligand purity is up to ~90% and can be done for a few thousand cells at a time.

This work can be expanded to quantify bound fraction for TCR-like antibodies targeting specific peptide/MHC ligands enriched from cell lysates of tumor samples, as a calibration step towards unknown tumor sample testing. Importantly, this technology is highly relevant to many cancers where validation of targeting is needed at the tumor protein level and only limited aspiration biopsy material is available, which is often the case.

Some advantages of the disclosed technology over existing approaches are that:
(1) The electric component of the sensor can pull complexes from a very low concentration solution into the optical trap-sensor without the user having to wait for an impractically long time for the complex to diffuse into the sensor. This allows using very low peptide-presenting ligand concentrations (down to few pM), enabling for the first time to use a few thousand cancer cells for screening targeted antibodies.
(2) The sensor is a heterogeneity filter that can identify the difference between an antibody-ligand complex versus unbound antigen-presenting ligands, unbound antibodies, or aggregates because: (a) when aggregates are trapped over the sensor they will create untypically large optical and electrical signal changes and we will use those bimodal signals to exclude them from binding measurements; and (b) in enriched peptide-presenting ligand solutions it is unlikely that non-specific binders will have nearly identical mass and charge signatures to true antibody binding events and therefore will be excluded also. As a result, this sensor will relax solution heterogeneity restrictions that hamper current screening approaches.
(3) Enable simultaneous electrical and optical sensing at the single molecule level that allows separating mass from effective charge estimates in individual proteins and complexes that they form without requiring expensive labeling techniques. Prior studies had to assume protein mass, and the resulting mass estimate bias would propagate into the effective charge estimate used to identify that a protein complex had formed.

A sensor as in Example 3 was assembled, including fabrication of a sensor chip.

To evaluate the sensor, several initial studies use purified MHC-peptide ligands and TCR-like antibodies. The following recombinant MHC/peptide ligands were synthesized and purified: HLA-A2/CEA, HLA-A2/p68, and HLA-A2/Her2. In brief, soluble MHC class I/peptide ligands was generated by overexpression of the HLA-A2 heavy chain and beta 2 microglobulin as recombinant proteins in *E. coli* and subsequent in vitro refolding and assembly in the presence of 10 mM of specific peptide. To obtain soluble MHC/peptide complexes the alpha-heavy chain (HC) sequence was mutagenized to remove the cytosolic and transmembrane regions. The material is then purified on a Superdex-75 column (GE) and fractions with the correctly refolded material are pooled and protein yield determined. The yields for these three HLA-A2-peptide ligands generally range from 4 to 10 mg per synthesis reaction. The TCR-like antibodies specific for the three HLA-peptide complexes that will be used in this application have been described previously.

Aliquots of the above-described pure protein solutions can be dispensed and mixed at different molar ratios in the bimodal sensor's PDMS chamber to demonstrate specific TCR-like antibody binding for cognate HLA-A2-peptide ligand. In brief, a range of concentrations of TCR-like antibodies can be used (up to 1 μM) and captured on the sensor. Next, a range of concentrations (up to 100 pM) of HLA-A2-peptides can be added to the sensor in PBS buffer. Specific versus non-specific interactions are assessed to make sure that a distinct signal to noise ratio is obtained using the purified material. It can be determined how data acquisition duration, limited by slow stage drift that leads to optical signal drift, impacts mass measurement accuracy. Statistical comparisons of fluctuation amplitudes with and without a trapped protein place the mass measurement limit at ~1 kDa. The disclosed sensor geometry can be used and the nanopore size and solution pH can be kept constant to study effective charge uncertainty and its dependence on mass measurement uncertainty. Calculations estimate a charge uncertainty of ~1e. This level of accuracy has been previously shown in non-polar solutions with a micron-scale optical-electrical sensor. Rejection of non-binding multi-protein trapping events can be attained by modulating the optical trap intensity at frequencies matching the transit time of proteins across the trap. The autocorrelation amplitude of signal fluctuations can indicate if more than one protein complex is in the trap. Non-bound proteins can also be verified by turning off the laser, forcing their translocation through the pore. The laser diode has very fast response, below 1 μs, which is smaller than the ~5 μs uncertainty of transit time measurement through the nanopore. The novel bimodal sensor enables determining independently the protein size from the optical signal and then estimate effective charge from the electrical signal. The bimodal sensor signatures are used to distinguish between antibody-ligand complexes versus individual unbound proteins trapped in the sensor.

Figure 14A:
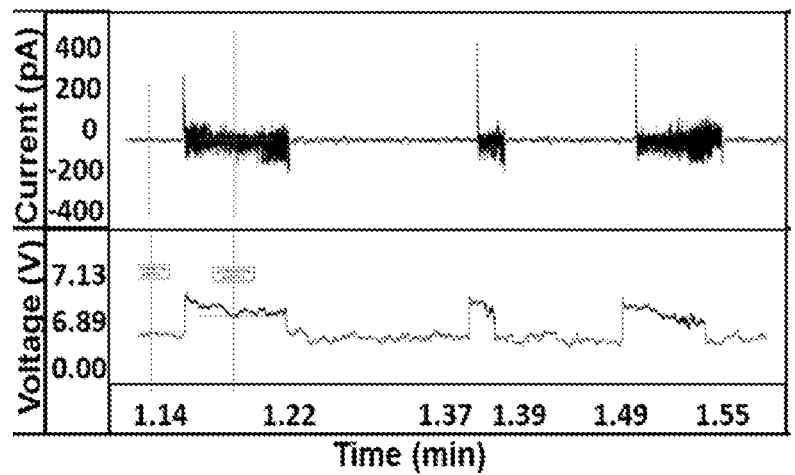
FIG. 14A is an electrical signal (top panel) and optical signal (bottom panel) for RAH H2Db antigen, showing three separate trapping events.
Figure 14B:
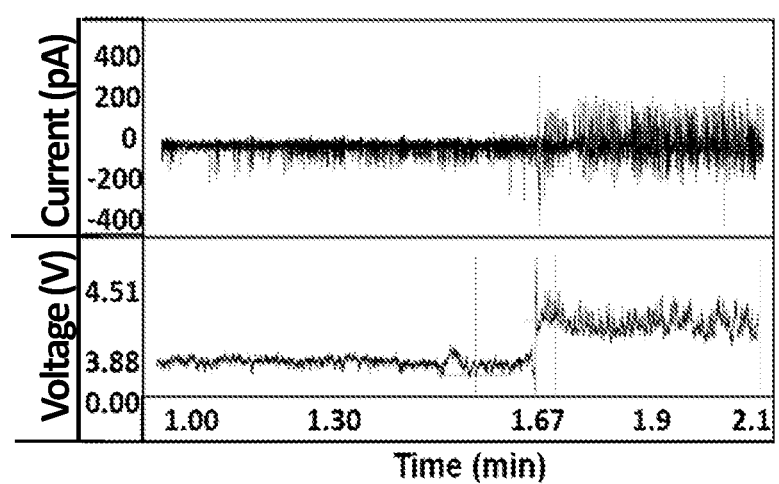
FIG. 14B is an electrical signal (top panel) and optical signal (bottom panel) of a trapping event for a monoclonal antibody targeting the RAH H2Db antigen.
Figure 14C:
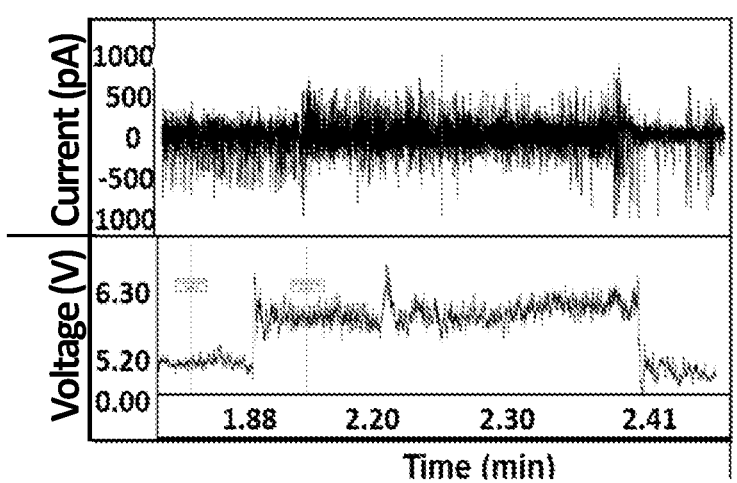
FIG. 14C is an electrical signal (top panel) and optical signal (bottom panel) of a trapping event for an antigen-antibody complex lasting ~31 seconds before the complex translocated through the sensor.

Proof of principle measurements for antibody-antigen (ligand) interactions are shown in FIG. 14. FIG. 14a shows three sequential trapping events for H2Db RAH antigens that are an MEW class I allotype from C57Blk/6 (mouse strain) analogous to HLA (Human). The RAHYNIVTF peptide from HPV 16 E7 protein induces T-cell response when presented by H2Db in the mouse. This HPV-induced peptide is common in ovarian cancers. FIG. 14b shows a trapping event for a monoclonal antibody (mAb) targeting this peptide-presenting antigen. FIG. 14c shows a trapping event for this mAb-antigen complex. Interestingly, the change in optical signal trapping was ~4% for the antigen (45 kDa), ~16% for the mAb (150 kDa) and ~21% for the antigen-antibody complex, which is roughly consistent with the known linear dependence of optical signal to protein size. Control experiments with a control West Nile virus peptide presented by H2Db did not yield significant mAb binding (not shown for brevity).

The Au layer deposited on top of the SANE sensor is conducting and provides some level of shielding from the applied voltage bias applied through the nanopore below it. Preliminary results above indicate that a balance between the electrical and optical forces is achieved, which creates multi-second trapping. However, it can further be determined which experimental parameters result in trapping durations long enough to identify a binding event, but short enough to maximize the throughput of proteins and protein complexes to be assessed. Parameters can be varied, including salt concentration, voltage bias and optical trapping power, to identify parameter combinations that result in trapping events that last long enough to be identifiable, which is currently estimated to be in the hundreds of milliseconds. To add an additional level of control on translocation time, a 10 nm layer of $SiO_2$ can be deposited on top of the Au layer. This layer can be added before the front side mask photoresist is deposited and the $SiO_2$ can be etched with ME before the Au and Cr wet etching step described in the Example 3, above. The added dielectric layer can enable more sensitive control of voltage bias across the senor. Software for analyzing the recorded time-series data can be developed to identify binding events. For the optical data, step-finding algorithms can be used that are a standard for identifying single molecule events in optical imaging. For the electrical data, open access algorithms can be adapted for analyzing nanopore translocation events. The bimodal sensor parameters attained from these analyses can be the optical signal step change, trapping duration, translocation current amplitude and nanopore translocation duration. Classification accuracy of binding events can be tested initially with the pure antibody-antigen solutions described above for a wide range of relative concentrations of reactants to identify the upper and lower bounds of each sensor signal value type that is consistent with a binding event.

The sensor can also be used to detect specific HLA-A2-peptide complexes from tumor cell lysates. Negative controls can include 1×104 tumor cells from T47D breast and Skov-3 ovarian cancer lines that do not express the particular HLA-A2-peptides targeted by the TCR-like antibodies. Initially, 1 ng of HLA-A2-peptide complex can be used to spike tumor lysate that will be followed by an enrichment step. Specifically, NiNTA agarose beads (Qiagen) coated with monoclonal antibody BB7.2 that binds to HLA-A2 can then be added to lysates to enrich for HLA-peptide complexes. A cloned and expressed pan-HLA-A2 antibody as a single-chain antibody containing a 6-his tag at the C-terminal end can be used to conjugate to the Ni-NTA beads. After a 30-minute incubation at room temperature, the NiNTA beads can be washed 2× with cold PBS buffer followed by a 5-minute incubation with 0.1M Imidazole buffer, pH10 to elute the BB7.2 antibody-HLA-A2/peptide complex. The enriched material can be added to the sensor's PDMS chamber containing the captured TCR-like antibodies and binding can be assessed. After establishing these conditions, the experiment can be repeated using a range of HLA-A2-peptide concentrations (up to 100 pM) and a lysate-only control. Based on experience with electrical-only nanopore sensing and the rapid switching speed possible for our laser trap, it is estimated that up to 10 molecules per second can be attracted from solution. It can be determined by subsequent off-line processing if each detected event corresponds to true antibody binding to peptide-presenting HLA, an aggregate, or unbound protein that translocated through the nanopore.

For the positive control experiments, 1×104 tumor cells that knowingly express the endogenous HLA-A2/peptide complex targeted by our TCR-like antibodies can be used. This scenario closely mimics the number of cells that would be collected from a biopsy aspirate as well as be representative to the naturally expressed number of copies on a tumor cell. These cells can be processed as were the negative controls above, and HLA-A2-complexes can be enriched using the NiNTA-BB7.2 coated beads. The HLA-A2/Her2 peptide positive (Sk-ov-3-A2, ovarian), the HLA-A2/p68 peptide complex positive (MDA-MD-231, breast) and the HLA-A2/CEA peptide complex positive (HCT-116, colon) cell lines can be tested.

The binding event identification algorithm as described above for pure protein solutions can be further tested and refined for enriched protein solutions. Comparisons with bimodal sensor signatures from pure protein data can be used for separating specific binding events from aggregates and non-specific binding events that are unlikely to have nearly identical optical and electrical signatures as true binding events.

Additional non-limiting, example embodiments are further described below.

Embodiment 1

A sensor comprising:
a first layer having at least one dual nanohole structure, and
a second layer having at least one nanopore,
wherein the dual nanohole structure comprises a first nanohole and a second nanohole connected by a gap; and
wherein the gap of the first layer is aligned with the nanopore of the second layer in a direction corresponding to a translocation direction across the first and second layers.

Embodiment 2

The sensor of Embodiment 1, wherein the first layer and the second layer are adhered together with an adhesion layer disposed between the first layer and the second layer.

Embodiment 3

The sensor of Embodiment 1 or Embodiment 2, wherein the first layer and the second layer define a chip of the sensor.

Embodiment 4

The sensor of any of the preceding Embodiments, wherein the first layer and/or the second layer is formed from an inorganic material.

Embodiment 5

The sensor of any of the preceding Embodiments, wherein the first layer is formed from a metal.

Embodiment 6

The sensor of Embodiment 5, wherein the first layer is formed from gold.

Embodiment 7

The sensor of any of the preceding Embodiments, wherein the second layer is formed from an electrically insulating material.

Embodiment 8

The sensor of Embodiment 7, wherein the second layer is formed from silicon nitride.

Embodiment 9

The sensor of any of the preceding Embodiments, wherein the first layer has an average thickness of up to 500 nm in the translocation direction.

Embodiment 10

The sensor of any of the preceding Embodiments, wherein the first layer has an average thickness of 50-150 nm in the translocation direction.

Embodiment 11

The sensor of any of the preceding Embodiments, wherein the second layer has an average thickness of up to 500 nm in the translocation direction.

Embodiment 12

The sensor of any of the preceding Embodiments, wherein the second layer has an average thickness of 30-120 nm in the translocation direction.

Embodiment 13

The sensor of any of the preceding Embodiments, wherein the nanoholes of the first layer have an average diameter in a direction perpendicular to the translocation direction of 80-120 nm.

Embodiment 14

The sensor of any of the preceding Embodiments, wherein the nanoholes have sloped interior walls along the translocation direction.

Embodiment 15

The sensor of Embodiment 14, wherein the sloped interior walls have a grade of 10-30%.

Embodiment 16

The sensor of any of the preceding Embodiments, wherein the nanoholes have a center-to-center separation distance of 150 nm or less.

Embodiment 17

The sensor of Embodiment 16, wherein the nanoholes overlap.

Embodiment 18

The sensor of any of the preceding Embodiments, wherein the gap has a width of 20-50 nm.

Embodiment 19

The sensor of any of the preceding Embodiments, wherein the gap has a width that is within 10% of a diameter of the nanopore.

Embodiment 20

The sensor of any of the preceding Embodiments, wherein the gap is continuous with the nanopore in the translocation direction.

Embodiment 21

The sensor of any of the preceding Embodiments, wherein the nanopore has a diameter of 10-30 nm.

Embodiment 22

The sensor of any of the preceding Embodiments further comprising a third layer defining a window.

Embodiment 23

The sensor of Embodiment 22, wherein the window is formed from silicon.

Embodiment 24

A method of sensing comprising:
providing a test sample comprising complexed and/or non-complexed biomolecules;
contacting the test sample with the first layer of the sensor of any of Embodiments 1-23; irradiating the dual nanohole structure of the first layer of the sensor with a beam of electromagnetic radiation;
   optically trapping the biomolecules in the dual nanohole structure and/or the gap of the first layer of the sensor and measuring a surface plasmon resonance of the dual nanohole structure;
   applying an electric field across the nanopore of the second layer of the sensor; and
   measuring change in current across the nanopore during one or more translocation events of the biomolecules.

Embodiment 25

The method of Embodiment 24, wherein optically trapping the biomolecules results in the surface plasmon resonance.

Embodiment 26

The method of Embodiment 24 or Embodiment 25, wherein measuring the surface plasmon resonance further comprises determining the mass of an optically trapped biomolecule.

Embodiment 27

The method of any of Embodiments 24-26, wherein applying an electric field includes temporarily reversing the electric field.

Embodiment 28

The method of any of Embodiments 24-27, wherein applying an electric field across the nanopore results in translocation events.

Embodiment 29

The method of any of Embodiments 24-28, wherein measuring change in current further comprises determining the charge of a translocating biomolecule.

Embodiment 30

The method of any of Embodiments 24-29, wherein the first layer and the second layer of the sensor are immediately adjacent layers.

Embodiment 31

A method of making a sensor, the method comprising:
providing a chip having a first layer and a second layer;
forming a dual nanohole structure in the first layer; and
forming a nanopore in the second layer;
wherein the dual nanohole structure comprises a first nanohole and a second nanohole connected by a gap, the gap being aligned with the nanopore of the second layer in a direction corresponding to a translocation direction across the first and second layers, and
wherein the dual nanohole structure extends through the first layer but does not extend into the second layer.

Embodiment 32

The method of Embodiment 31, wherein forming the dual nanohole structure comprises forming the first nanohole and forming the second nanohole sequentially or simultaneously.

Embodiment 33

The method of Embodiment 32, wherein forming the second nanohole comprises overlapping the second nanohole with the first nanohole.

Embodiment 34

The method of Embodiment 32 or Embodiment 33, wherein forming the second nanohole further comprises forming the gap.

Embodiment 35

The method of any of Embodiments 31-33, wherein forming the nanopore further comprises forming the gap.

Embodiment 36

The method of any of Embodiments 31-33, wherein forming the nanopore further comprises increasing a length and/or width of the gap.

Embodiment 37

The sensor of Embodiments 1-30, wherein the first layer is non-continuous.

Embodiment 38

The sensor of Embodiments 1-31 and 37, wherein the first layer comprises one or more holes in addition to the at least one dual nanohole structure.

Embodiment 39

The sensor of Embodiments 1-31 and 37-38 further comprising a third layer formed from an electrically insulating material.

Embodiment 40

The method of Embodiments 31-36 further comprising forming one or more additional holes in the first layer.

Embodiment 41

The method of Embodiments 31-36 and 40, wherein forming the one or more additional holes comprises forming one or more islands of first layer material and the dual nanohole structure is positioned on an island.

Embodiment 42

The method of Embodiments 31-36 and 40-41, wherein the island having the dual nanohole structure has an area of 1 µm²-10 mm².

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A sensor comprising:
   a first layer having at least one dual nanohole structure, and
   a second layer having at least one nanopore,
   wherein the dual nanohole structure comprises a first nanohole and a second nanohole connected by a gap;
   wherein the gap of the first layer is aligned with the nanopore of the second layer in a direction corresponding to a translocation direction across the first and second layers;
   wherein the gap has a width of 10-50 nm; and
   wherein the at least one nanopore entirely passes through the second layer in the translocation direction.

2. The sensor of claim 1, wherein the first layer and the second layer are adhered together with an adhesion layer disposed between the first layer and the second layer.

3. The sensor of claim 1, wherein the first layer and the second layer define a chip of the sensor.

4. The sensor of claim 1, wherein the first layer and/or the second layer is formed from an inorganic material.

5. The sensor of claim 1, wherein the first layer is formed from a metal.

6. The sensor of claim 5, wherein the first layer is formed from gold.

7. The sensor of claim 1, wherein the first layer is not continuous.

8. The sensor of claim 1, wherein the first layer comprises one or more holes in addition to the at least one dual nanohole structure.

9. The sensor of claim 1, wherein the second layer is formed from an electrically insulating material.

10. The sensor of claim 1, wherein the nanoholes of the first layer have an average diameter in a direction perpendicular to the translocation direction of 80-120 nm.

11. The sensor of claim 1, wherein the nanoholes have sloped interior walls along the translocation direction.

12. The sensor of claim 1, wherein:
   the sensor further comprises a third layer beneath the first layer and the second layer;
   the third layer defines a window; and
   the window of the third layer is wider than the nanopore of the second layer.

13. A method of sensing comprising:
   providing a test sample comprising complexed and/or non-complexed biomolecules;
   contacting the test sample with the first layer of the sensor of claim 1;
   irradiating the dual nanohole structure of the first layer of the sensor with a beam of electromagnetic radiation;
   optically trapping the biomolecules in the dual nanohole structure and/or the gap of the first layer of the sensor and measuring a surface plasmon resonance of the dual nanohole structure;
   applying an electric field across the nanopore of the second layer of the sensor; and
   measuring change in current across the nanopore during one or more translocation events of the biomolecules.

14. The method of claim 13, wherein optically trapping the biomolecules results in the surface plasmon resonance.

15. The method of claim 13, wherein measuring surface plasmon resonance further comprises determining the mass of an optically trapped biomolecule.

16. The method of claim 13, wherein applying an electric field includes temporarily reversing the electric field.

17. The method of claim 13, wherein applying an electric field across the nanopore results in the one or more translocation events.

18. The method of claim 13, wherein measuring change in current further comprises determining the charge of a translocating biomolecule.

19. The method of claim 13, wherein the first layer and the second layer of the sensor are immediately adjacent layers.

20. A method of making a sensor, the method comprising:
   providing a chip having a first layer and a second layer;
   forming a dual nanohole structure in the first layer; and
   forming a nanopore in the second layer;
   wherein the dual nanohole structure comprises a first nanohole and a second nanohole connected by a gap, the gap being aligned with the nanopore of the second layer in a direction corresponding to a translocation direction across the first and second layers,
   wherein the dual nanohole structure extends through the first layer but does not extend into the second layer;
   wherein the gap has a width of 10-50 nm; and
   wherein the nanopore entirely passes through the second layer in the translocation direction.

* * * * *